US008058503B1

(12) United States Patent　　(10) Patent No.: US 8,058,503 B1
Langham　　(45) Date of Patent: Nov. 15, 2011

(54) NON-DEHISCENT PYGMY SESAME VARIETY SESACO 70

(75) Inventor: Derald Ray Langham, San Antonio, TX (US)

(73) Assignee: Sesaco Corporation, Fallbrook, CA (US)

(*) Notice: Subject to any disclaimer, the term of this patent is extended or adjusted under 35 U.S.C. 154(b) by 15 days.

(21) Appl. No.: 12/769,495

(22) Filed: Apr. 28, 2010

(51) Int. Cl.
*A01H 1/00* (2006.01)
*A01H 5/00* (2006.01)
*A01H 5/10* (2006.01)
*C12N 5/04* (2006.01)

(52) U.S. Cl. ........ 800/260; 800/296; 800/298; 435/430; 435/430.1

(58) Field of Classification Search .................. None
See application file for complete search history.

(56) References Cited

U.S. PATENT DOCUMENTS

| 6,100,452 | A | 8/2000 | Langham | |
|---|---|---|---|---|
| 6,781,031 | B2 | 8/2004 | Langham | |
| 6,815,576 | B2 | 11/2004 | Langham | |
| 7,148,403 | B2 | 12/2006 | Langham | |
| 7,332,652 | B2 | 2/2008 | Langham | |
| 2006/0230472 | A1* | 10/2006 | Langham | 800/295 |

FOREIGN PATENT DOCUMENTS

| WO | WO9915681 | 4/1999 |
|---|---|---|
| WO | WO0013488 | 3/2000 |

OTHER PUBLICATIONS

Ashri, A. 2007. Sesame (*Sesamum indicum* L.). In: R.J. Singh, Ed. Genetic Resources, Chromosome Engineering and Crop Improvement, vol. 4, Oilseed Crops, p. 231-289, CRC Press, Boca Raton, FL, US.
Ashri, A.1998."Sesame Breeding," Plant Breeding Rev. 16:179-228.
Ashri, A. 1980. "Sesame," Oil Crops of the World, Chap. 18, pp. 375-387; McGraw-Hill Publishing, Co., New York.
Bakheit, et al. 1996. "Inheritance of Some Qualitative and Quantitative Characters in *Sesamum idicum* L," Assuit Journal of the Agricultural Sciences 27:27-41.
Day, Jamie. 1998 "The mechanism of indehiscence in Sesame. Features that might be useful in a breeding programme," Third FAO/IAEA Research Coordination meeting on Induced Mutations for Sesame Improvements, Bangkok, Thailand; Apr. 6-19, 1998; 11pp.
Delgado, et al. 1992. "Analisis Del Cruzamiento Dialelico De Seis Variedades Indehiscentes Y Dos Dehiscentes de Ajonjoli *Sesamum indicum* L." Agronomia Tropical 42:191-210.
Hutson, B.D. 1983. "Standards for the inspection and grading of sesame seed," Hutson Laboratories, Yuma, Arizona, pp. 1-5.
IBPGR Secretariat. 1981. "Descriptors for Sesame," International Board for Plant Genetic Resources, Rome, pp. 1-19.
Kalton, R.R. 1949. "A promising new oilseed crop for Texas," Proc First International Sesame Conference, Clemson Agricultural College, Clemson, South Carolina, pp. 62-66.

Langham, D.R. 2007. "Phenology of Sesame," Issues in New Crops and New Uses, Janick & Whipkey, eds., ASHS Press, Alexandria, VA, pp. 144-182.
Langham, D.G. 1944. "Natural and controlled pollination in sesame," Journal of Heredity 8:254-256.
Langham, D.G. and Rodriguez, J. 1949. "Improvements in Sesame in Venezuela," Proc. First Intern'l Sesame Conf., Clemson Agri. College, Clemson, South Carolina, pp. 74-79.
Langham, et al. 1956. "Dehiscencia Y otras caracteristicas del ajonjoli, *Sesamum indicum* L., en relacion con el problema de la cosecha," Gensa, Maracay, Venezuela; pp. 3-16.
Langham, D.R. 1998. "Shatter resistance in Sesame," Third FAO/IAEA Res. Co-ord. Mtng on Induced Mutations for Sesame Improvements, Bangkok, Thailand, Apr. 6-10, 1998; 14 pages.
Langham, D.R. 2001. "Shatter resistance in sesame," in: L. Van Zanten (ed.), Sesame improvements by induced mutations, Proc. Final FAO/IAEA Coordination Research Meeting, IAEA, Vienna TECDOC 1195, pp. 51-61.
Langham, D.R. & Wimers, T. 2002. "Progress in mechanizing sesame in the U.S. through breeding," Trends in Crops and New Uses, J. Janick & A. Whipkey (eds.), ASHA Press, Alexandria, VA, pp. 157-173.
Namiki, Mitsuo. 1995. "The Chemistry and Physiological Functions of Sesame," Food Reviews International, 11:281-329.
Osman, H.E. 1985. "Studies in sesame: hybridization and related techiniques," FAO Plant Production and Protection Paper No. 66, pp. 145-156.
"Recommendations for the Discussion Groups," 1995. Proceedings of Sesame Workshop, Darwin and Katherine, Northern Territory, Australia, Mar. 12-23, 1995, pp. 252-257.
Shigeo, et al. 1994. "Breeding of good quality sesame with dehiscence resistance and strong antioxidative property," Baiorunessansu Keikaku (abstract only).
Wongyai, W. & Juttpornpong, S. 1992 Indirect selection for seed weight in sesame using capsule size as a criteria, Sesame and Safflower Newsletter, No. 7, pp. 4-7.
Weiss, E.A. 1971. "History," Castor, Sesame and Safflower, Leonard-Hill Books, London; pp. 311-525.
Weiss, E.A. 1983. "Sesame," Oilseed Crops, Longman Inc., New York, pp. 282-340.
Weiss. 2000. "Sesame," Oilseed Crops, Longman Inc., New York, pp. 131-164.
Yermanos, D.M. 1980. "Sesame," Hybridization of Crop Plants, American Society of Agronomy—Crop Science of America, Madison, Wisconsin, pp. 549-563.
Yermanos, D.M. 1984. "Sesame growing: an idealized overview," Text of speech given in Cairo, Egypt, 4 pages.
Zanten, L. Van (ed.) 1996. "Conclusions and Recommendations," 2nd FAO/IAEA Research Coordination Meeting, Antalya, Turkey, pp. 107-113.

* cited by examiner

*Primary Examiner* — Vinod Kumar
(74) *Attorney, Agent, or Firm* — Eugenia S. Hansen; Hemingway & Hansen, LLP

(57) ABSTRACT

Pygmy sesame line (*Sesamum indicum* L.) having a homozygous allele (py/py) and improved non-dehiscence (IND) is disclosed. A variety thereof (py/py) sesame designated Sesaco 70 (S70) is herein disclosed. Its degree of shatter resistance, or seed retention, makes S70 suitable for mechanized harvesting.

9 Claims, 11 Drawing Sheets

US 8,058,503 B1

NON-DEHISCENT PYGMY SESAME VARIETY SESACO 70

CROSS REFERENCE TO RELATED APPLICATIONS

Not applicable.

STATEMENT REGARDING FEDERALLY SPONSORED RESEARCH OR DEVELOPMENT

Not applicable.

TECHNICAL FIELD

This invention relates to a new pygmy *Sesamum indicum* L. variety with improved non-dehiscence appropriate for mechanized harvesting.

BACKGROUND OF THE INVENTION

Sesame, or *Sesamum indicum*, is a tropical annual cultivated worldwide for its oil and its nut flavored seeds. The sesame plant grows to a height of about 52-249 cm, and at its leaf axils are found capsules which contain the sesame seed. Upon maturity in nature, the capsules holding the sesame seeds begin to dry down, the capsules normally split open, and the seeds fall out. Commercially, the harvester tries to recover as much seed as possible from mature capsules. From ancient times through the present, the opening of the capsule has been the major factor in attempting to successfully collect the seed. Harvesting methods, weather, and plant characteristics all contribute to the amount of seed recovered.

The majority of the world's sesame is harvested manually. With manual non-mechanized methods, it is desirable for the sesame seed to fall readily from the plant. Manual harvesting is labor intensive. Efforts to mechanize or partially mechanize harvesting met with limited success.

A breakthrough was accomplished when non-dehiscent (ND) sesame was developed and patented by Derald Ray Langham. ND sesame was found to possess the proper characteristics which would enable mechanical harvesting without the seed loss disadvantages reported with prior varieties.

U.S. Pat. Nos. 6,100,452, 6,815,576, 6,781,031, 7,148,403, and 7,332,652 each disclose and claim non-dehiscent sesame cultivars having various characteristics.

An improved non-dehiscent sesame (IND) class of sesame was later developed by Derald Ray Langham. IND sesame, through increased constriction, better adhesion between the false membranes, and improved placenta attachment, holds more seed than prior sesame types, as measured four weeks after a crop is ready for harvest (could have been combined). The IND characteristics offer advantages for certain growing applications.

U.S. patent application Ser. No. 12/041,257, filed Mar. 3, 2008 discloses a method for breeding improved non-dehiscent sesame (IND). U.S. patent application Ser. No. 12/041,205, filed Mar. 3, 2008 discloses an improved non-dehiscent sesame cultivar S32, representative seed having been deposited under ATCC accession number PTA-8888. S32 is a stable, commercially suitable sesame line providing improved non-dehiscence, higher yield, and shorter drydown phase.

U.S. patent application Ser. No. 12/049,705, filed Mar. 17, 2008 discloses an improved non-dehiscent sesame cultivar S30, representative seed having been deposited under ATCC accession number PTA-8887. S30 is a stable, commercially suitable sesame line providing improved non-dehiscence, higher yield, and shorter drydown phase.

U.S. patent application Ser. No. 12/533,972, filed Jul. 31, 2009 discloses an improved non-dehiscent sesame cultivar S27, representative seed having been deposited under ATCC accession number PTA-10184. S27 is a stable, commercially suitable sesame line providing improved non-dehiscence, higher yield, and shorter drydown phase.

U.S. patent application Ser. No. 12/565,095, filed Sep. 23, 2009 discloses a non-dehiscent black sesame cultivar S55, representative seed having been deposited under ATCC accession number PTA-10185. S55 is a stable, commercially suitable sesame line providing the only black sesame that can be mechanically harvested.

Although sesame plants which are shorter than about 110 cm have been developed in order to attempt to increase the harvest index (the weight of the seed divided by the weight of the plant to include the seed), heretofore no known sesame plant in this height range exhibited ND or IND characteristics. Without ND or IND characteristics, shorter sesame plants have to be manually harvested. Such shorter plants present a disadvantage in manual harvesting because the worker has to bend over further to make a cut below the lowest capsule.

SUMMARY OF THE INVENTION

In one aspect, the invention comprises a pygmy sesame line having a (py/py) allele and improved non-dehiscence.

In one aspect, the invention comprises a seed of sesame variety designated Sesaco 70 (S70), a sample of said seed having been deposited under ATCC Accession No. PTA-9272.

BRIEF DESCRIPTION OF THE DRAWINGS

FIG. 2 depicts a comparison of the percent of seed retention during Shaker Shatter Resistance testing from 1997 to 2008.

FIG. 3 depicts a comparison of the mean improved non-dehiscent visual rating in Uvalde, Tex., and Lorenzo, Tex., in 2008.

FIG. 4 depicts a comparison of the plant architecture in terms of Height of the First Capsule and Capsule Zone Length in Uvalde, Tex., in 2008.

FIG. 5 depicts a comparison of the Average Internode Length within Capsule Zone in Uvalde, Tex., in 2008.

FIG. 6 depicts a comparison of the number of capsule node pairs in Uvalde, Tex., in 2008.

FIG. 7 depicts a comparison of the composite kill resistance ratings in Uvalde, Tex., in 2008.

FIG. 8 depicts a comparison of the mean days to physiological maturity in Uvalde, Tex., in 2008.

FIG. 9 depicts a comparison of the yield at drydown in Uvalde, Tex., and Lorenzo, Tex., in 2008.

FIG. 10 depicts a comparison of the mean weight of 100 seeds in grams from 1997 to 2008.

FIG. 11 depicts a comparison of the lodging resistance rating in Uvalde, Tex., in 2007.

DETAILED DESCRIPTION

Figure 1:
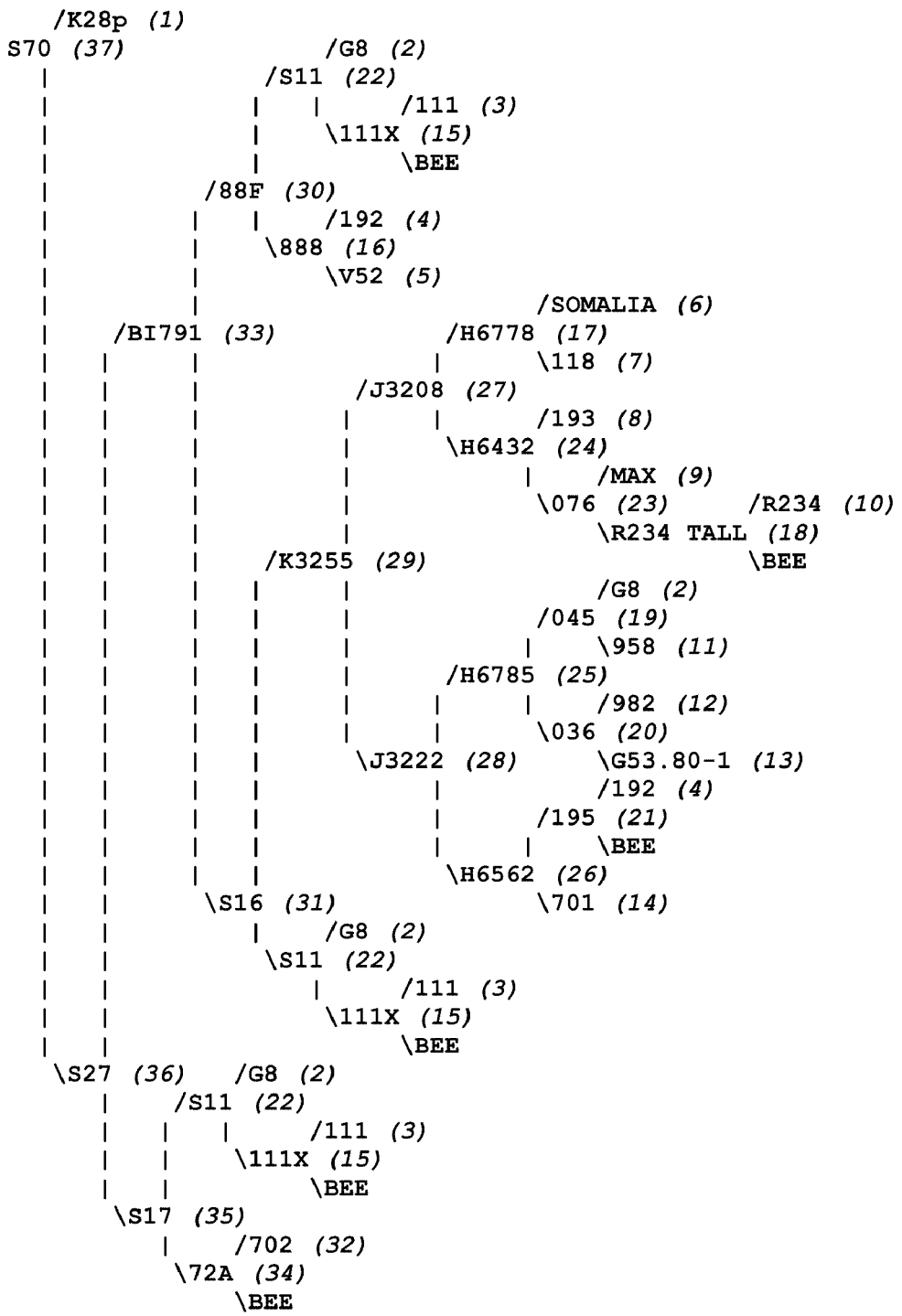
FIG. 1 depicts the lineage of S70.

Herein disclosed is a new pygmy sesame variety designated Sesaco 70 (S70), which is homozygous for a pygmy allele (py/py) and exhibits improved non-dehiscence (IND), rendering it suitable for mechanical harvesting. The "pygmy" sesame described averages approximately 85 cm in height, but the height may be somewhat greater than 85 cm or less than 85 cm depending on the environment. The height measurement is made after the plants stop flowering.

The height of pygmy sesame is dependent on several environmental factors, including the amount of moisture, heat, fertility, and population. Higher values for moisture, heat and fertility generally influence an increase in height. In a high population, the height will only increase if there is adequate fertility and moisture; otherwise, the height will be shorter. In low light intensities, the plants are generally taller. In the field, the range of heights for pygmy sesame is generally 52 to 110 cm.

Pygmy IND as disclosed herein is distinguishable from sesame heretofore described as "dwarf" varieties (described in Japan, China and Korea). "Pygmy" IND is homozygous for a pygmy allele (py/py) and has a shorter HEIGHT OF THE PLANT (Character No. 5 in Table II), a lower HEIGHT OF THE FIRST CAPSULE (Character No. 6 in Table II), and a shorter AVERAGE INTERNODE LENGTH WITHIN CAPSULE ZONE (Character No. 9 in Table II) than all known varieties released and grown commercially in the world.

A pure pygmy line can be proved by crossing the line with a known pygmy (py/py). If all of the plants in the F1 of the cross with the known pygmy exhibit a short height, low first capsule height, and short internode, the pygmy line in question is pure py/py. This is because the pygmy allele in a heterozygous condition (PY/py) does not exhibit the shorter height, lower first capsule, or shorter internode. In other words, heterozygous (PY/py) of the F1 generation, do not exhibit any intermediate characters. Height, first capsule height, and internode length are similar to the normal parent without the pygmy allele.

The pygmy sesame line of the invention can be planted using close row spacing without exhibiting spindly stems which are generally exhibited by other varieties planted in close row spacing. Pygmy sesame has a shorter AVERAGE INTERNODE LENGTH WITHIN CAPSULE ZONE which keeps the plants from exhibiting spindly stems, in comparison to prior varieties. By "close row spacing" it is meant that the rows are between about 15 to about 30 cm apart, whereas standard row spacing is between about 76 and about 102 cm apart. The ability to grow in close row spacing without exhibiting spindly stems prevents or inhibits lodging of the plants. The shorter height presents less of a profile to wind, and there is less lodging pressure. In addition, there are lower wind speeds closer to the ground.

Close row spacing is advantageous because the plants provide a canopy more rapidly, thereby inhibiting weed growth. Weeds are "shaded out" by a canopy because weeds sprouting from the ground under the canopy die or are stunted from the lack of sunlight. By planting in closer row spacing, the farmer has lower inputs (e.g. lower resources that are used in farm production, such as chemicals, equipment, feed, seed, and energy) since he does not have to cultivate (weed). Pygmy sesame planted in 15 to 20 cm rows can be used in a method of sesame agriculture which omits the step of cultivation. Omitting the cultivation is advantageous in that it reduces the growing costs since cultivation requires fuel (diesel), operator hours, and maintenance.

The pygmy sesame line of the invention can also thrive with more plants per linear meter and make the practice of overplanting more productive. Farmers generally engage in the practice of overplanting in order to ensure the maximum production of their acreage. If normal height sesame is planted, and the overplanting results in more than 10 plants per linear meter, some plants will shade out others. The shaded plants either die out, resulting in self-thinning, or survive as "minor plants" as defined in Langham, D. R. 2007. "Phenology of sesame," In: J. Janick and A. Whipkey (ed.), Issues in New Crops and New Uses, ASHS Press, Alexandria, Va. The minor plants do not produce a commensurate amount of seed for the moisture and nutrients that the minor plants use. In contrast, when pygmy sesame according to the invention is overplanted, less shading occurs with a high population within a row. The minor plants are more productive.

The pygmy sesame of the invention also exhibits IND which allows mechanical harvesting. The shorter height of the pygmy sesame IND as compared with other IND provides an advantage in harvesting. Shorter plants are easier to combine with modern equipment because the reel does not push the plants forward before pulling them into the combine header. As a result there is less shatter loss and fewer plants that are pushed forward under the header. Within the combine header, the pygmy plants do not bridge over the auger as do taller varieties. In addition, by having a higher harvest index it is easier to separate the sesame from the trash in the combine.

Pygmy sesame lines have shown higher yields than existing varieties in low input conditions (less moisture and/or fertility) because they expend fewer resources making stems and leaves and use the scarce resources in making seed.

In the subsequent paragraphs, further detail about the pygmy sesame line of the invention and comparisons with other sesame lines is provided.

Sesame plants have been studied for their response to seasonal and climatic changes and the environment in which they live during the different phases and stages of growth and development. This type of study, called "phenology" has been documented by the inventor in Langham, D. R. 2007. "Phenology of sesame," In: J. Janick and A. Whipkey (ed.), *Issues in New Crops and New Uses*, ASHS Press, Alexandria, Va., referenced supra.

Table I summarizes the phases and stages of sesame, and will be useful in describing the present invention.

TABLE I

Phases and stages of sesame

| Stage/Phase | Abbreviation | End point of stage | DAP[z] | No. weeks |
|---|---|---|---|---|
| Vegetative | VG | | | |
| Germination | GR | Emergence | 0-5 | 1– |
| Seedling | SD | $3^{rd}$ pair true leaf length = $2^{nd}$ | 6-25 | 3– |
| Juvenile | JV | First buds | 26-37 | 1+ |
| Pre-reproductive | PP | 50% open flowers | 38-44 | 1– |
| Reproductive | RP | | | |
| Early bloom | EB | 5 node pairs of capsules | 45-52 | 1 |
| Mid bloom | MB | Branches/minor plants stop flowering | 53-81 | 4 |
| Late bloom | LB | 90% of plants with no open flowers | 82-90 | 1+ |
| Ripening | RI | Physiological maturity (PM) | 91-106 | 2+ |
| Drying | DR | | | |
| Full maturity | FM | All seed mature | 107-112 | 1– |
| Initial drydown | ID | $1^{st}$ dry capsules | 113-126 | 2 |
| Late drydown | LD | Full drydown | 127-146 | 3 |

[z]DAP = days after planting. These numbers are based on S26 in 2004 Uvalde, Texas, under irrigation.

There are several concepts and terms that are used in this document that should be defined. In the initial drydown stage in Table I, the capsules begin to dry and open. This stage ends when 10% of the plants have one or more dry capsules. The late drydown stage ends when the plants are dry enough so that upon harvest, the seed has a moisture of 6% or less. At this point some of the capsules have been dry for 5 weeks in the example used in Table I, but in other environments for other varieties, the drying can stretch to 7 weeks. The "ideal harvest time" is at the end of the late drying stage. At this point, a combine (also sometimes referred to as a combine harvester, a machine that combines the tasks of harvesting, threshing, and cleaning grain crops) can be used to cut and thresh the plants and separate the seed from the undesired plant material. However, at times, weather may prevent harvest at the ideal time. The plants may have to remain in the field for as much as an additional four weeks, and in some cases even longer. Thus, time $t_0$ corresponds to the ideal harvest time and time $t_1$, which corresponds to the time the grower actually harvests the sesame is a time later than time $t_0$.

Sesame cultivar Sesaco 70 (hereinafter "S70") is a variety which exhibits Improved Non-Dehiscence (IND) characteristics and desirable characteristics which make it a commercially suitable sesame line. IND characteristics are defined in comparison to non-dehiscence (ND) characteristics first described and defined by the inventor in U.S. Pat. No. 6,100,452. Compared to ND sesame, IND sesame has more seed in the capsules when measured between 4 and 9 weeks after the ideal harvest time.

Without wishing to be bound by one particular theory, it is believed that this increased amount of seed in the capsules is may be due to the IND variety having the ability to better withstand adverse environmental conditions such as inclement or harsh weather. Examples of adverse weather conditions as to which IND has been subjected to in this regard are rain, fog, dew, and wind. S70 variety has been tested and meets the criteria of IND.

Filed and commonly owned U.S. patent application Ser. No. 12/041,257, filed Mar. 3, 2008 is herein incorporated by reference as if fully set forth herein. This application discloses Improved Non-Dehiscent Sesame and the present invention. S70 is an example of a variety which resulted from breeding methods described therein. Concurrently filed and commonly owned U.S. patent application Ser. No. 12/769,475, is herein incorporated by reference as if fully set forth herein. This patent discloses Pygmy Sesame Plants for Mechanical Harvesting and the present invention. S70 is an example of a variety which resulted from breeding methods described therein.

S70 exhibits improved shatter resistance, acceptable resistance to common fungal diseases, and a maturity that allows a wide geographical range. Further, S70 exhibits higher yield in geographical locations desirable for sesame planting, and exhibits desirable seed size and seed color. S70 is suitable for planting in areas that have approximately a 21° C. ground temperature when planted in the spring and night temperatures above 5° C. for normal termination. An exemplary desirable geographical area for S70 is from South Texas at the Rio Grande to southern Kansas and from east Texas westward to elevations below 1,000 meters.

Other exemplary areas are areas of the United States or of the world which areas have similar climatic conditions and elevations.

The pedigree method of plant breeding was used to develop S70. Sesame is generally self-pollinated. Crossing is done using standard techniques as delineated in Yermanos, D. M. 1980. "Sesame. Hybridization of crop plants," *Am Soc Agronomy-Crop Sci of America*, pp. 549-563 and U.S. Pat. No. 6,100,452. Ashri provides an overview of sesame breeding in Ashri, A. (1998). "Sesame breeding," *Plant Breed. Rev.* 16:179-228 and Ashri, A. 2007. Sesame (*Sesamum indicum* L.). In: R. J. Singh, Ed., Genetic Resources, Chromosome Engineering, and Crop Improvement, Vol. 4, Oilseed Crops, p. 231-289, CRC Press, Boca Raton, Fla., USA.

The lineage of S70 is presented in FIG. 1.

K28p (1) was a line obtained from Churl Kahn from the Republic of Korea in 1992 and first planted in the Gilleland nursery (Uvalde, Tex.) in 1993. Within Sesaco, K28 first carried the identifier 1838 and was later changed to TK28 and then to TK28p.

G8 (2) was a line obtained from D. G. Langham in 1977 and first planted by Sesaco in the Kamman nursery (Wellton, Ariz.) in 1978. It was a selection from the cultivar 'Guacara' which D. G. Langham developed in Venezuela in the 1950s. Guacara was an initial selection from a cross that later produced one of the major varieties in Venezuela—Aceitera. Within Sesaco, G8 first carried the identifier X011 and was later changed to TG8.

111 (3) was a line obtained from the NPGS (PI173955) in 1979 and first planted by Sesaco in the Woods nursery (Wellton, Ariz.) in 1981. NPGS obtained it in 1949 from W. N. Koelz, USDA, Beltsville, Md. who obtained it from India. Within Sesaco, 111 first carried the identifier 0858 and was then changed to X111. In 1985, a selection of this line became Sesaco 4 (S04).

192 (4) was a line obtained from the M. L. Kinman in 1980 and first planted by Sesaco in the Woods nursery (Wellton, Ariz.) in 1981. The line was originally T61429-B-4-1-3 from the Kinman USDA sesame program, College Station, Tex., which had been in cold storage at Ft. Collins, Colo. In 1997, the line was transferred to the NPGS, Griffin, Ga. and given the identifier PI599462. Within Sesaco, 192 first carried the identifier 1479 and then was changed to X191 and X193. In 1985, a selection from X193 became Sesaco 3 (S03) and a selection of X191 became Sesaco 7 (S07).

V52 (5) was a cultivar designated as SF075 obtained from the Sesamum Foundation (D. G. Langham, Fallbrook, Calif.) collection in 1977 and first planted by Sesaco in the Kamman nursery (Wellton, Ariz.) in 1978. The Sesamum Foundation obtained it from B. Mazzani (Maracay, Venezuela) in 1960. Originally, it was a cultivar known as Venezuela 52 developed by D. G. Langham in the 1940s. Within Sesaco, V52 first carried the identifier 0075 and was later changed to TV52.

SOMALIA (6) was a line obtained from the NGPS (PI210687) in 1979 and first planted in Kamman nursery (Wellton, Ariz.) in 1979. The NGPS obtained it from the Administrazione Fiduciaria Italiana della Somalia, Mogadishu, Somalia. Within Sesaco, it carried the identifier 0730.

118 (7) was a line obtained from the NGPS (PI425944) in 1979 and first planted in Kamman nursery (Wellton, Ariz.) in 1979. The NGPS obtained it in 1978 from P. F. Knowles, University of California, Davis, Calif., who collected it in Pakistan. Within Sesaco, it carried the identifier 1118 and then changed to X118 and then to T118.

193 (8) was a selection from 192 which was a line obtained from the M. L. Kinman in 1980 and first planted by Sesaco in the Woods nursery (Wellton, Ariz.) in 1981. The line was originally T61429-B-4-1-3 from the Kinman USDA sesame program, College Station, Tex., which had been in cold storage at Ft. Collins, Colo. In 1997, the line was transferred to the NPGS, Griffin, Ga. and given the identifier PI599462. Within Sesaco, 192 first carried the identifier 1479 and then was changed to X191 and X193. In 1985, a selection from X193 became Sesaco 3 (S03) and a selection of X191 became Sesaco 7 (S07).

MAX (9) was a line designated as SF116 obtained from the Sesamum Foundation (D. G. Langham, Fallbrook, Calif.) in 1977 and first planted in the Kamman nursery (Wellton, Ariz.) in 1978. The Sesamum Foundation obtained it from Maximo Rodriguez in 1961. He had collected it from Mexico where it was known as Instituto Regional Canasta. Within Sesaco, it carried the identifier 0116 and then changed to TMAX.

R234 (10) was a named variety obtained from D. M. Yermanos in 1978 from his sesame program at the University of California at Riverside. It was first planted in the Kamman nursery (Wellton, Ariz.) in 1978. Within Sesaco, it carried the identifier 0544 and then changed to T234.

958 (11) was a line obtained from the Sesamum Foundation in 1977 and first planted in the Kamman nursery (Wellton, Ariz.) in 1978. It was obtained with a designator of SF411 and was named G958-1. The Sesamum Foundation obtained it from John Martin in 1962 who had obtained it from the D. G. Langham breeding program in Venezuela. Within Sesaco, G958-1 carried the identifier 0411.

982 (12) was a line obtained from the Sesamum Foundation in 1977 and first planted in the Kamman nursery (Wellton, Ariz.) in 1978. It was obtained with a designator of SF477 and was named G53.98-2. The Sesamum Foundation obtained it from John Martin in 1962 who had obtained it from the D. G. Langham breeding program in Venezuela. G53.98-2 was a cross made by D. G. Langham in 1953 in Guacara, Venezuela. Within Sesaco, 982 carried the identifier 0477 and then changed to T982.

G53.80-1 (13) was a line obtained from the Sesamum Foundation in 1977 and first planted in the Kamman nursery (Wellton, Ariz.) in 1978. It was obtained with a designator of SF471. The Sesamum Foundation obtained it from John Martin in 1962 who had obtained it from the D. G. Langham breeding program in Venezuela. G53.80-1 was a cross made by D. G. Langham in 1953 in Guacara, Venezuela. Within Sesaco, G53.80-1 carried the identifier 0471.

701 (14) was a line obtained from the NGPS (PI292145) in 1979 and first planted in Woods nursery (Wellton, Ariz.) in 1981. The NGPS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from the Indian subcontinent. Within Sesaco, it carried the identifier 0701 and then changed to X701. In 1984, a selection from X701 became Sesaco 5 (S05).

111X (15) was an outcross in the 111 (2) plot BT0458 in the Nickerson nursery (Yuma, Ariz.) in 1982. Within Sesaco, it carried the identifier E0745 and later changed to T111X.

888 (16) was a cross between 192 (4) and V52 (5) made by Sesaco in the Nickerson nursery (Yuma, Ariz.) in 1982. Within Sesaco, 888 first carried the identifier F888 and then changed to T888.

H6778 (17) was a cross between Somalia (6) and 118 (7) made by Sesaco in the Hancock nursery (Wellton, Ariz.) in 1984. Within Sesaco, it carried the identifier H6778.

R234 TALL (18) was an outcross in the R234 (10) strip in the Kamman nursery (Wellton, Ariz.) in 1979. Within Sesaco, it carried the identifier X026.

045 (19) was a cross between G8 (2) and 958 (11) made by Sesaco in the Kamman nursery (Wellton, Ariz.) in 1978. Within Sesaco, it carried the identifier B045 and then changed to T045.

036 (20) was a cross between 982 (12) and G53.80-1 (13) made by Sesaco in the Kamman nursery (Wellton, Ariz.) in 1979. Within Sesaco, it carried the identifier C036 and then X036. In 1984, a selection from X036 became Sesaco 6 (S06).

195 (21) was an outcross selected in the 192 (4) in plot MN4584 in the McElhaney nursery (Wellton, Ariz.) in 1983. Within Sesaco, it carried the identifier E0690 and then changed to X195.

S11 (22) was a cross between G8 (2) and 111X (15) made by Sesaco in the Nickerson nursery (Yuma, Ariz.) in 1982. Within Sesaco, it has carried the identifier F804; in 1988, a selection of this line became Sesaco 11 (S11).

076 (23) was a cross between MAX (9) and R234 TALL (18) made by Sesaco in the Kamman nursery (Wellton, Ariz.) in 1979. Within Sesaco, it carried the identifier C076 and then changed to T076.

H6432 (24) was a cross between 193 (8) and 076 (23) made between by Sesaco in the Hancock nursery (Wellton, Ariz.) in 1984. Within Sesaco, it carried the identifier H6432.

H6785 (25) was a cross between 045 (19) and 036 (20) made by Sesaco in the Hancock nursery (Wellton, Ariz.) in 1984. Within Sesaco, it carried the identifier H6785.

H6562 (26) was a cross between 195 (21) and 701 (14) made by Sesaco in the Hancock nursery (Wellton, Ariz.) in 1984. Within Sesaco, it carried the identifier H6562.

J3208 (27) was a cross between H6778 (17) and H6432 (24) made by Sesaco in the Hancock nursery (Wellton, Ariz.) in 1985. Within Sesaco, it carried the identifier J3208.

J3222 (28) was a cross between H6785 (25) and H6562 (26) made by Sesaco in the Hancock nursery (Wellton, Ariz.) in 1985. Within Sesaco, it carried the identifier J3222.

K3255 (29) was a cross between J3208 (27) and J3222 (28) made by Sesaco in the Hancock nursery (Wellton, Ariz.) in 1986. Within Sesaco, it carried the identifier K3255.

88F (30) was a cross between S11 (22) and 888 (16) made by Sesaco in the Sharp nursery (Roll, Ariz.) in 1988. Within Sesaco, it carried the identifier LCE01 and then changed to X88F and then T88F.

S16 (31) was a cross between K3255 (29) and S11 (22) made by Sesaco in the Wright nursery (Roll, Ariz.) in 1987. Within Sesaco, it carried the identifier KAP11 and then changed to XFXA. In 1991, a selection from XFXA became Sesaco 16 (S16).

702 (32) was a line obtained from the NGPS (PI292146) in 1979 and first planted in Woods nursery (Wellton, Ariz.) in 1981. The NGPS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from the Indian subcontinent. Within Sesaco, it has carried the identifier 0702.

BI791 (33) was a cross between 88F (30) and S16 (31) made by Sesaco in the Gilleland nursery (Uvalde, Tex.) in 1992. Within Sesaco, it carried the identifier BI791.

72A (34) was an outcross selected in the 702 (15) strip SL2140 in the Ramsey nursery in 1984. Within Sesaco, it carried the identifier X702A and then T72A.

S17 (35) was a cross between S11 (22) and 72A (34) made by Sesaco in the Wright nursery (Roll, Ariz.) in 1987. Within Sesaco, it carried the identifier KAN22 and then changed to X7AB. In 1992, a selection from X7AB because Sesaco 17 (S17).

S27 (36) was a cross between BI791 (33) and S17 (35) made by Sesaco in the Friesenhahn nursery (Knippa, Tex.) in 1994. Within Sesaco, it carried the identifier, CM586 and then changed to X88K. A selection became Sesaco 27 (S27).

S70 (37) was a cross between K28p (1) and S27 (36) made by Sesaco in the Gilleland nursery (Uvalde, Tex.) in Year 1 (hereinafter "Year" is abbreviated as "YR"). The original designator was KK654.

The seed (K654) was planted in plot XR05 in the Schwartz nursery (Wall, Tex.) in YR2. Two plants were selected because they had a good internode length.

The seed of one of the plants (0471) was planted in plot 2470 in the Panther City nursery (Batesville, Tex.) in YR3. Two volunteer plants from seed that had fallen from the plot were selected based on hold on a very low plant at the end of the nursery.

The seed from one of the plants (3623) was planted in plot D018 in the Chapman nursery (Lorenzo, Tex.) in YR4. The designator was changed to dK654. One plant was selected based on final hold at the end of the nursery, a long capsule zone on a short plant, and very good lodging after winds over 50 MPH.

The seed from this plant (1804) was planted in plot B501 in the Chapman nursery in YR5. Two bulks were selected based on being taller than sister selections, very low plant height with a short internode length, and good hold at the end of the nursery.

The seed from these bulks (2209, and 2286) were planted in 2 plots (WE01 and WE04) in the Gilleland nursery and 2 plots (D001 and D004) in the Chapman nursery in YR6. Four bulks were selected from these 4 plots based on having excellent hold on the last day of the nurseries. The designator was changed to XD55p.

The seed from these four bulks were planted in strips (VF54n through VF71n) in the Gilleland nursery in YR7. Most of the seed from these strips was harvested for testing in farmer fields.

The materials were bulked and planted on farmer experimental fields for testing under commercial conditions in 2008. The seed was designated S70.

Along with breeding programs, tissue culture of sesame is currently being practiced in such areas of the world as Korea, Japan, China, India, Sri Lanka and the United States. One of ordinary skill in the art may utilize sesame plants grown from tissue culture as parental lines in the production of nondehiscent sesame. Further IND sesame may be propagated through tissue culture methods. By means well known in the art, sesame plants can be regenerated from tissue culture having all the physiological and morphological characteristics of the source plant.

The present invention includes the seed of sesame variety S70 deposited under ATCC Accession No. PTA-9272; a sesame plant or parts thereof produced by growing the seed deposited under ATCC Accession No. PTA-9272; sesame plants having all the physiological and morphological characteristics of sesame variety S70; and sesame plants having all the physiological and morphological characteristics of a sesame plant produced by growing the seed deposited under ATCC Accession No. PTA-9272. The present invention also includes a tissue culture of regenerable cells produced from the seed having been deposited under ATCC Accession No. PTA-9272 or a tissue culture of regenerable cells from sesame variety S70 or a part thereof produced by growing the seed of sesame variety S70 having been deposited under ATCC Accession No. PTA-9272. A sesame plant regenerated from a tissue culture of regenerable cells produced from the seed having been deposited under ATCC Accession No. PTA-9272 or from sesame variety S70, wherein the regenerated sesame plant has all the physiological and morphological characteristics of sesame variety S70 is also contemplated by the present invention. Methods of producing sesame seed, comprising crossing a first parent sesame plant with a second parent sesame plant, wherein the first or second parent sesame plant was produced by seed having been deposited under ATCC Patent Deposit Designation No. PTA-9272 is part of the present invention.

Unless otherwise stated, as used herein, the term plant includes plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like. Further, unless otherwise stated, as used herein, the term progeny includes plants derived from plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like.

Sesame cultivar S70 has been tested experimentally over several years under various growing conditions ranging from South Texas to Northern Texas. Sesame cultivar S70 has shown uniformity and stability within the limits of environmental influence for the characters listed in Table II below. Table II provides the name, definition, and rating scale of each character as well as the method by which the character is measured. Under the rating section, the rating for S70 is presented in bold text. Additionally, the distribution of the character in Sesaco's sesame development program is indicated under the rating section. Sesaco uses slightly different character specifications from "Descriptors for sesame", AGP: IBPGR/80/71, IBPGR Secretariat, Rome, (1981) and from the form "Sesame (*Sesamum indicum*)", U.S. Department of Agriculture Plant Variety Protection Office, Beltsville, Md. The descriptors in those documents were developed in the early 1980s and have not been updated to incorporate new concepts in sesame data collection.

Table II provides characteristics of S70 for forty-four (44) traits. Numerical ratings and values reported in this table were experimentally determined for S70 with prior sesame varieties in side by side replicated trials. Actual numerical values and ratings for a given variety will vary according to the environment, and the values and ratings provided in Table II were obtained in the environment specified in the parenthetical following the S70 rating. Tables IV and V provide a direct comparison between the new S70 variety and the prior varieties thus demonstrating the relative differences between the varieties in the side by side trials.

TABLE II

Characters Distinguishing the S70 Line

| Character | Rating | Methodology |
|---|---|---|
| (1) BRANCHING STYLE The potential amount of true branching in a line | S70 genotype = B S70 phenotype = U (All crops, all nurseries) Subjective rating based on the following values: U = Uniculm—no | The amount of branching on any particular plant depends on the space around the plant. In high populations, branching can be suppressed. This rating should be based on potential as expressed on end plants and plants in the open. |

TABLE II-continued

Characters Distinguishing the S70 Line

| Character | Rating | Methodology |
|---|---|---|
| | branching except weak branches in open<br>B = True branches<br>When S70 is crossed with other uniculm lines without pygmy alleles (py/py) (Character No. 10), there will be branching in the F1 generation. This indicates that S70 has branching genes that are not expressed because little light reaches the junction of the petiole to the stem where branches emerge. Thus, S70 has a branching genotype but a uniculm phenotype.<br>Distribution within Sesaco based on stable lines in the crossing program in 1982-2001 (Total number of samples tested = 1,333)<br>U = 42.4%<br>B = 57.6% | True branches start in the leaf axil below the first flower, and they begin to emerge before the first open flower. As long as there is light into the leaf axils, there will be additional branches that start below the first branches in subsequently lower nodes. Weak branches occur when a plant is in the open. They develop in the lowest node pairs and subsequent branches start at higher nodes. There are lines that will not branch in any circumstance.<br>Some lines in the open will put on spontaneous branches late in the cycle. True and weak branches do not have a capsule in the same leaf axil, whereas the spontaneous branches form under the capsule after the capsule has formed. Spontaneous branches are not counted as branches.<br>There are rare lines where the flowering pattern is to put on flowers on lower nodes late in the cycle. In this case, the capsule is formed after the branch is developed. This pattern should not be termed spontaneous branching, and the branch is normally counted as a true branch.<br>There are branched lines that have secondary branches on the branches. In a few cases, there can be tertiary branches. Additional branches generally appear in low populations.<br>COMMENTS: the effects of light appear to have more of an effect on branching than moisture and fertility. High populations suppress branching. There must be light to the growing tip in order for a branch to develop. |
| (2) NUMBER OF CAPSULES PER LEAF AXIL<br>The predominant number of capsules per leaf axil in the middle half of the capsule zone | S70 = 1<br>(All crops, all nurseries)<br>Subjective rating based on the following values:<br>1 = Single<br>3 = Triple<br>Based on potential as described in the methodology presented herein<br>Distribution within Sesaco based on stable lines in the crossing program in 1982-2001<br>(Total number of samples tested = 1,327)<br>1 = 58.3%<br>3 = 41.7% | Rating can be taken from about 60 days after planting through to the end of the crop.<br>NUMBER OF CAPSULES PER LEAF AXIL is highly dependent on moisture, fertility, and light. In triple capsule lines, the central capsule forms first, and axillary capsules follow a few days later. Triple capsule lines have the potential to put on axillaries, but will not do so if plants do not have adequate moisture and/or fertility. In drought conditions, some triple capsule lines will produce only a central capsule for many nodes. In these lines, when there is adequate moisture through rain or irrigation, some will add axillary capsules on only new nodes, while others will add axillary capsules to all nodes. Some triple capsule lines will not put on axillary capsules if there is no direct sunlight on the leaf axil. To date, lines with single capsules have nectaries next to the central capsule in the middle of the capsule zone while triple capsules do not. However, some lines have what appear to be nectaries on the lower capsules of triple lines, but upon close examination, they are buds which may or may not eventually develop into a flower and then a capsule. In most triple capsule lines, the lower and upper nodes have single capsules. There are some lines where the end plants can put on 5 capsules/leaf axil and a few that have the potential to put on 7 capsules/leaf axil. 5 and 7 capsules only appear with open plants with high moisture and fertility. In some environments, single capsule lines will put on multiple capsules on 1 node and |

TABLE II-continued

Characters Distinguishing the S70 Line

| Character | Rating | Methodology |
|---|---|---|
| (3) MATURITY CLASS The maturity of a line in relation to a standard line. Currently, the standard line is S26 at 99 days | S70 = M for 98 days (Uvalde nursery<sup>a,</sup> 2005-2008) Subjective rating based on the following values: V = Very early (<85 days) E = Early (85-94 days) M = Medium (95-104 days) L = Late (105-114 days) T = Very late (>114 days) Distribution within Sesaco based on stable lines in the crossing program in 1998-2001 (Total number of samples tested = 650) V = 1.2% E = 26.8% M = 56.2% L = 12.9% T = 2.9% | rarely on up to 5 nodes. These lines are not considered triple capsule lines. The basis for this data point is DAYS TO PHYSIOLOGICAL MATURITY (Character No. 30). S24 was the standard line to be used to compute MATURITY CLASS in previous patents. In 1998-2001, the maturity of S24 averaged 95 days in the Uvalde, TX, nursery. Through 2006, the standard was adjusted using S24. S26 was selected to establish a new standard. In 2001-2006 S26 averaged 4 days longer than S24. For each line, the physiological maturity for each year is subtracted by the S26 maturity for that year in that nursery, and then the number of days of difference is averaged. The average is then added to 99. See DAYS TO PHYSIOLOGICAL MATURITY (Character No. 30) for the effects of the environment on MATURITY CLASS. |
| (4) PLANT PHENOTYPE A three character designation that provides the branching style, number of capsules per leaf axil, and the maturity class | S70 = U1M (phenotype) (All crops; all nurseries) Subjective rating based on the following values: BRANCHING STYLE U = Uniculm—no branching except weak branches in open B = True branches NUMBER OF CAPSULES PER LEAF AXIL 1 = Single 3 = Triple MATURITY CLASS V = Very early (<85 days) E = Early (85-94 days) M = Medium (95-104 days) L = Late (105-114 days) T = Very late (>114 days) Distribution within Sesaco based on stable lines in the crossing program in 1998-2001 (Total number of samples tested = 650) U1V = 0% U3V = 1.1% U1E = 3.8% U3E = 8.3% U1M = 16.0% U3M = 12.0% U1L = 3.4% U3L = 2.2% U1T = 0.5% U3T = 0.6% B1V = 0% B3V = 0.2% B1E = 8.0% B3E = 6.3% B1M = 23.2% B3M = 4.8% B1L = 6.5% B3L = 1.0% B1T = 1.6% B3T = 0.4% | The first character is the BRANCHING STYLE (Character No. 1), followed by the NUMBER OF CAPSULES PER LEAF AXIL (Character No. 2), and then the MATURITY CLASS (Character No. 3). When these characters are placed in a matrix, there are 20 potential phenotypes. The phenotype provides an overview of the general appearance of the plant. There is a very high correlation between MATURITY CLASS and HEIGHT OF PLANT (Character No. 5). |
| (5) HEIGHT OF PLANT The height of the plant from the ground to the top of the highest capsule with viable seed | S70 = 85 cm (Uvalde nursery, 2008) Value based on the average of a minimum of three plants (unit of measure: cm) Distribution within Sesaco based on stable lines in the crossing program in 1999-2001 (Total number of samples tested = 2,274) low = 56 cm; high = 249 cm 1 = <94.6 cm; 5.2% 2 = <133.2 cm; 34.6% 3 = <171.8 cm; 54.9% 4 = <210.4 cm; 5.1% 5 = >210.3 cm; 0.1% | The measurement is made after the plants stop flowering. For plants that are not erect or have lodged, the plant should be picked up for the measurement. In most lines the highest capsule is on the main stem. In lines with the dt/dt alleles (determinate), the highest capsule is on the branches. COMMENTS: this height is dependent on the amount of moisture, heat, fertility, and population. Increased values generally increase the height. In a high population, the height will only increase if there is adequate fertility and moisture; otherwise, the height will be shorter. In low light intensities, the heights are generally taller. |

TABLE II-continued

Characters Distinguishing the S70 Line

| Character | Rating | Methodology |
|---|---|---|
| (6) HEIGHT OF FIRST CAPSULE<br>The height of the first capsule from the ground to the bottom of the lowest capsule on the main stem | avg. = 134.8 cm, std = 23.5<br>S70 = 27 cm (Uvalde nursery, 2008)<br>Value based on an the average of a minimum of three plants (unit of measure: cm)<br>Distribution within Sesaco based on stable lines in the crossing program in 1999-2001 (Total number of samples tested = 2,274)<br>low = 20 cm; high = 193 cm<br>1 = <54.6 cm; 52.7%<br>2 = <89.2 cm; 45.5%<br>3 = <123.8 cm; 1.5%<br>4 = <158.4 cm; 0.3%<br>5 = >158.3 cm; 0.1%<br>avg. = 54.2 cm, std = 14.3 | The measurement is made after the plants stop flowering. For plants that are not erect or have lodged, the plant should be picked up for the measurement. In most lines, the lowest capsule is on the main stem. True branches have capsules higher than on the main stem except when the flowers fall off the main stem. Occasionally, on weak branches, the lowest capsule is on the branches. There are lines that flower in the lower nodes late in the cycle, and thus, the measurement should be taken after flowering ends. In many lines the first flower does not make a capsule, and thus, this height may not be the same as the height of the first flower.<br>COMMENTS: see HEIGHT OF PLANT (Character No. 5) for effects of environmental factors |
| (7) CAPSULE ZONE LENGTH<br>The length of the capsule zone. The capsule zone extends from the bottom of the lowest capsule on the main stem to the top of the highest capsule with viable on the main stem. | S70 = 58 cm (Uvalde nursery, 2008)<br>Value based on an the average of a minimum of three plants (unit of measure: cm)<br>Distribution within Sesaco based on stable lines in the crossing program in 1999-2001 (Total number of samples tested = 2,274)<br>low = 18 cm; high = 188 cm<br>1 = <52 cm; 4.7%<br>2 = <86 cm; 53.5%<br>3 = <120 cm; 41.3%<br>4 = <154 cm; 0.5%<br>5 = >153.9 cm; 0.1%<br>avg. = 80.6 cm, std = 17.2 | The measurement is derived by subtracting the HEIGHT OF FIRST CAPSULE (Character No. 6) from the HEIGHT OF PLANT (Character No. 5).<br>COMMENTS: see HEIGHT OF PLANT (Character No. 5) for effects of environmental factors |
| (8) NUMBER OF CAPSULE NODE PAIRS<br>The number of capsule node pairs from the lowest capsule node to the highest node with capsules with viable seed on the main stem of the plant | S70 = 28 pairs (Uvalde nursery, 2008)<br>Value based on an the average of a minimum of three plants (unit of measure: number )<br>Distribution within Sesaco based on stable lines in the crossing program in 1999-2001<br>of samples tested = 2154)<br>low = 10; high = 54<br>1 = <18.8; 17.9%<br>2 = <27.6; 48.3%<br>3 = <36.4; 29.5%<br>4 = <45.2; 3.6%<br>5 = >45.1; 0.7%<br>avg. = 25.3, std = 6.4 | The count is made after the plants stop flowering. On opposite and alternate arranged leaves, each pair of leaves is counted as one node pair. In some lines, there are three leaves per node for at least part of the plant, and those are counted as one node pair. In some plants, flowers may not have produced capsules on one or more of the leaf axils in a node. These node pairs should still be counted. Node pairs on the branches are not counted. In years when the amount of moisture available to the plant is irregular, node pairs can become very irregular, particularly on triple capsule lines. In the upper portions of the plant, it may become easier to count the capsule clusters and divide by 2. While it is possible to count node pairs after leaves have fallen, it is much easier to count while the leaves are still on the plant.<br>COMMENTS: the number of node pairs is dependent on the amount of moisture and fertility. Higher moisture and fertility increases the number of node pairs. |
| (9) AVERAGE INTERNODE LENGTH WITHIN CAPSULE ZONE<br>The average internode length within the capsule zone | S70 = 2.1 cm (Uvalde nursery, 2007)<br>Value based on an the average of a minimum of three plants (unit of measure: cm)<br>Distribution within Sesaco based on stable lines in the crossing program in 1999-2001 (Total number | Divide the CAPSULE ZONE LENGTH (Character No. 7) by the NUMBER OF CAPSULE NODE PAIRS (Character No. 8).<br>COMMENTS: this length is dependent on the amount of moisture, fertility, and population. Increased values generally increase the length. In a high population, the length will only increase if there is adequate fertility and moisture; otherwise |

TABLE II-continued

Characters Distinguishing the S70 Line

| Character | Rating | Methodology |
|---|---|---|
| | of samples tested = 2145) <br> low = 1.09 cm; high = 8.09 cm <br> 1 = <2.49 cm; 6.2% <br> 2 = <3.89 cm; 74.6% <br> 3 = <5.29 cm; 18.6% <br> 4 = <6.69 cm; 0.4% <br> 5 = >6.68 cm; 0.1% <br> avg. = 3.35 cm, std = 0.66 | the length will be shorter. In low light intensities, the lengths are generally longer. <br> Past methodologies have measured the internode length at the middle of the capsule zone. Some have measured it at the median node and others at the median CAPSULE ZONE LENGTH. |
| (10) PRESENCE OF PYGMY ALLELES <br> The pygmy allele is a new recessive gene that affects the growth of the sesame plant. | S70 = py/py <br> (All crops; all nurseries) <br> py/py = homozygous pygmy alleles <br> PY/py = heterozygous pygmy alleles <br> PY/PY = normal (no pygmy alleles) <br> Distribution within Sesaco based on stable lines in the collection as of 2009 (Total number of lines = 40,715) <br> py/py = 145 <br> PY/py = 629 <br> Normal = 39,941 | In the homogygous condition. the pygmy allele (py) reduces the HEIGHT OF THE PLANT (Character No. 5), the HEIGHT OF THE FIRST CAPSULE (Character No. 6), and the AVERAGE INTERNODE LENGTH WITHIN CAPSULE ZONE (Character No. 9). In the heterozygous state, there are no reductions in the characters. In a cross between a homozygous pygmy and a normal, the pygmy allele is a recessive gene that will not show the shorter heights and internode lengths until segregating in the F2 generation, with no intermediates between the pygmy and the normal line. A homozygous pygmy selected in the F2, from the F3 generation on is pure in its effects on the three characters. Within pygmy lines there are differences in the 3 characters, but all of the pygmies differ from the normal lines. The name "pygmy" was chosen because these lines are shorter than dwarf lines that have been in the world germplasm for many years. The dwarf lines share the same three characters, but there are intermediates in the F2 generation and rarely any plants as short as the original dwarf. |
| (11) YIELD AT DRYDOWN <br> An extrapolation of the yield of a field by taking sample yields | S70 = 1,220 kg/ha <br> (Uvalde nursery, 2008) <br> S70 = 742 kg/ha <br> (Lorenzo nursery, 2008)[b] <br> Values based on the average of a minimum of three replications (unit of measure: kg/ha) <br> Distribution within Sesaco based on stable lines in the crossing program in 1999-2001 (Total number of samples tested = 1,828) <br> low = 67 kg/ha <br> high = 2421 kg/ha <br> 1 = <537.8 kg/ha; 5.6% <br> 2 = <1008.6 kg/ha; 15.6% <br> 3 = <1479.4 kg/ha; 51.5% <br> 4 = <1950.2 kg/ha; 25.8% <br> 5 = >1950.1 kg/ha; 1.4% <br> avg. = 1114.6 kg/ha, <br> std = 331.2 | On 3 replicated plots, when the plants are dry enough for direct harvest, cut a minimum of 1/5,000 of a hectare in the plot (Sesaco uses 1/2620), and place the plants in a cloth bag. Thresh the sample in a plot thresher and weigh the seed. Multiply the weight by the appropriate multiplier based on area taken to provide the extrapolated yield in kg/ha. <br> In the Almaco thresher there is about 3% trash left in the seed. Since yields are comparative, there is no cleaning of the seed done before the computation. If other threshers have more trash, the seed should be cleaned before weighing. <br> COMMENTS: yields increase with moisture and fertility. However, too high a moisture can lead to killing of plants. Too high fertility can lead to extra vegetative growth that may not lead to higher yields. The optimum population depends on the PLANT PHENOTYPE, Character No. 4 (BRANCHING STYLE, Character No. 1; NUMBER OF CAPSULES PER LEAF AXIL, Character No. 2; and MATURITY CLASS, Character No. 3) and row width. |
| (12) RESISTANCE TO DROUGHT <br> The relative amount of resistance to drought | S70 No data collected <br> In general, pygmies appear to exhibit more drought resistance than normal lines, but S70 specifically has not yet been rated and compared to other patented varieties. <br> Average of a minimum of three plots of a subjective rating based on the following values: <br> 0 to 8 scale <br> 7 = Little effect from | In a year when there is a drought, this rating can be used to differentiate the effects of the different lines. This is a highly subjective rating requiring a rater that is familiar with the performance of the line under normal conditions. The rating is based on how the drought changes the line from normal. Thus, a short line that does not change significantly in a drought may have a higher rating than a tall line which is affected by the drought even though the taller line is taller in the drought than the short line. |

TABLE II-continued

Characters Distinguishing the S70 Line

| Character | Rating | Methodology |
|---|---|---|
| | drought<br>4 = Medium effect from drought<br>1 = Considerable effect from drought<br>Intermediate values are used.<br>When there are limited ratings across varieties within one nursery in replicated plots, varieties can be compared with the general terms:<br>Good<br>Average<br>Poor<br>Distribution within Sesaco based on stable lines in he crossing program in 2000 (Total number of samples tested = 632)<br>low = 0; high = 8<br>1 = <1.6; 0.8%<br>2 = <3.2; 28.0%<br>3 = <4.8; 36.1%<br>4 = <6.4; 34.5%<br>5 = >6.3; 0.6%<br>avg. = 4.1, std = 1.2 | |
| (13) LEAF LENGTH<br>The length of the leaf blade from the base of the petiole to the apex of the leaf from the 5$^{th}$, 10$^{th}$, and 15$^{th}$ node pairs | S70 = 14.3 cm for 5$^{th}$ node pair; 15.6 cm for 10$^{th}$ node pair; and 13.6 cm for 15$^{th}$ node pair (Uvalde nursery, 2008)<br>Value based on an the average of a minimum of three plants (unit of measure: cm)<br>Distribution within Sesaco for 5$^{th}$ leaf based on stable lines in the crossing program in 2002 (Total number of lines tested = 196 with 711 samples)<br>low = 13.8 cm; high = 42.5 cm<br>1 = <19.5 cm; 34.7%<br>2 = <25.3 cm; 48.0%<br>3 = <31.0 cm; 14.3%<br>4 = <36.8 cm; 1.5%<br>5 = >36.7 cm; 1.5%<br>avg. = 21.5 cm, std = 4.4<br>Distribution within Sesaco for 10$^{th}$ leaf based on stable lines in the crossing program in 2002 (Total number of lines tested = 196 with 711 samples)<br>low = 9.3 cm; high = 32.9 cm<br>1 = <14.0 cm; 22.4%<br>2 = <18.7 cm; 41.8%<br>3 = <23.5 cm; 20.9%<br>4 = <28.2 cm; 10.2%<br>5 = >28.1 cm; 4.6%<br>avg. =17.9 cm, std = 4.8<br>Distribution within Sesaco for 15$^{th}$ leaf based on stable lines in the crossing program in 2002 (Total number of lines tested = 196 with 711 samples)<br>low = 4.4 cm; high = 26.2 cm<br>1 = <8.8 cm; 5.1%<br>2 = <13.1 cm; 42.9%<br>3 = <17.5 cm; 29.8% | Select one leaf per node to measure from the 5$^{th}$, 10$^{th}$, and 15$^{th}$ node pairs from the base of the plant. All the leaves for one line should be collected at the same time. Some lines retain the cotyledons, and the cotyledon node does not count as a node pair. In some lines the lowest leaves abscise leaving a scar on the stem. Abscised node pairs should be counted. In lines with alternate leaves, one node is counted for each pair of leaves. In some lines in parts of the plant there are three leaves per node which should be counted as one node pair.<br>The leaves continue growing in the first few days after they have separated from the growing tip. The choosing of leaves should be done a minimum of 5 days after the 15$^{th}$ node has appeared. Timing is important, because the plants will begin to shed their lower leaves towards the end of their cycle.<br>There are lines that have less than 15 node pairs. In this case, the highest node should be taken and the node number annotated to the measurements.<br>There can be as much as 6 mm difference between a green leaf and a dry leaf. The measurements can be done on a green or dry leaf as long as any comparison data with other lines is based on the same method.<br>Generally, the lowest leaves increase in size until the 4$^{th}$ to 6$^{th}$ node and then they decrease in size. This applies to LEAF LENGTH (Character No. 13), LEAF BLADE WIDTH (Character No. 15), and PETIOLE LENGTH (Character No. 16). In few cases, LEAF BLADE LENGTH Character No. 14) can increase up the 10$^{th}$ node, but will decrease by the 15$^{th}$ node. Generally, the width will decrease at a greater rate than the length.<br>COMMENTS: the length is dependent on the amount of moisture and fertility. Higher moisture and fertility increase the length. Leaf size also appears to be affected by light intensity. In Korea, the |

TABLE II-continued

Characters Distinguishing the S70 Line

| Character | Rating | Methodology |
|---|---|---|
| | 4 = <21.8 cm; 15.8%<br>5 = >21.7 cm; 6.6%<br>avg. = 14.3 cm, std = 4.2 | Korean lines have much larger leaves than in Oklahoma. In Korea, there is more cloud cover and a general haze than in Oklahoma. |
| (14) LEAF BLADE LENGTH<br>The length of the leaf blade from the base of the leaf blade to the apex of the leaf from the $5^{th}$, $10^{th}$, and $15^{th}$ node pairs | S70 = 10.2 cm for $5^{th}$ node pair; 13.2 cm for $10^{th}$ node pair; and 11.5 cm for $15^{th}$ node pair (Uvalde nursery, 2008) Value based on an the average of a minimum of three plants (unit of measure: cm)<br>Distribution within Sesaco for $5^{th}$ leaf based on stable lines in the crossing program in 2002 (Total number of lines tested = 196 with 711 samples)<br>low = 9.0 cm; high = 25.5 cm<br>1 = <12.3 cm; 14.3%<br>2 = <15.6 cm; 60.2%<br>3 = <18.9 cm; 20.9%<br>4 = <22.2 cm; 3.1%<br>5 = >22.1 cm; 1.5%<br>avg. = 14.4 cm, std = 2.4<br>Distribution within Sesaco for $10^{th}$ leaf based on stable lines in the crossing program in 2002 (Total number of lines tested = 196 with 711 samples)<br>low = 8.3 cm; high = 23.4 cm<br>1 = <11.3 cm; 18.9%<br>2 = <14.3 cm; 42.9%<br>3 = <17.4 cm; 25.0%<br>4 = <20.4 cm; 9.2%<br>5 = >20.3 cm; 4.1%<br>avg. = 13.9 cm, std = 3.0<br>Distribution within Sesaco for $15^{th}$ leaf based on stable lines in the crossing program in 2002 (Total number of lines tested = 196 with 711 samples)<br>low = 4.2 cm; high = 20.7 cm<br>1 = <7.5 cm; 2.0%<br>2 = <10.8 cm; 36.7%<br>3 = <14.1 cm; 37.8%<br>4 = <17.4 cm; 16.3%<br>5 = >17.3 cm; 7.1%<br>avg. = 12.0 cm, std = 3.0 | See LEAF LENGTH (Character No. 13) on how to collect leaves. In some leaves the blade on one side of the petiole starts before the other side. This measure should start from the lowest blade side. There are leaves that have enations where a blade starts and then stops. The enations are not considered part of the leaf blade because they are very irregular from plant to plant and within a plant.<br>COMMENTS: see LEAF LENGTH (Character No. 13) for effects of environment |
| (15) LEAF BLADE WIDTH<br>The width of the leaf blade measured across the leaf blade at the widest point at the $5^{th}$, $10^{th}$, and $15^{th}$ node pairs | S70 = 6.0 cm for $5^{th}$ node pair; 3.3 cm for $10^{th}$ node pair; and 2.2 cm for $15^{th}$ node pair in 2008 (Uvalde nursery, 2008) Value based on an the average of a minimum of three plants (unit of measure: cm)<br>Distribution within Sesaco for $5^{th}$ leaf based on stable lines in the crossing program in 2002 (Total number of lines tested = 196 with 711 samples)<br>low = 3.4 cm; high = 31.0 cm<br>1 = <8.9 cm; 53.1%<br>2 = <14.4 cm; 33.7%<br>3 = <20.0 cm; 9.7%<br>4 = <25.5 cm; 2.6% | See LEAF LENGTH (Character No. 13) on how to collect leaves. There are many leaves that are not symmetrical with lobbing on one side and not the other. The width should still be measured across the widest point on a line perpendicular to the main vein of the leaf.<br>On some lines the width exceeds the length, particularly on lobed leaves.<br>COMMENTS: see LEAF LENGTH (Character No. 13) for effects of environment<br>The widest leaves are lobed. Normally, the leaves have turned from lobed to lanceolate by the $10^{th}$ leaf with the exception of the tropical lines. |

TABLE II-continued

Characters Distinguishing the S70 Line

| Character | Rating | Methodology |
|---|---|---|
| | 5 = >25.4 cm; 1.0%<br>avg. = 9.6 cm, std = 4.3<br>Distribution within Sesaco<br>for 10$^{th}$ leaf based on<br>stable lines in the crossing<br>program in 2002 (Total<br>number of lines tested =<br>196 with 711 samples)<br>low = 1.3 cm; high = 17.6<br>cm<br>1 = <4.6 cm; 69.4%<br>2 = <7.8 cm; 25.0%<br>3 = <11.1 cm; 4.6%<br>4 = <14.3 cm; 0%<br>5 = >14.2 cm; 1.0%<br>avg. = 4.3 cm, std = 2.2<br>Distribution within Sesaco<br>for 15$^{th}$ leaf based on<br>stable lines in the crossing<br>program in 2002 (Total<br>number of lines tested =<br>196 with 711 samples)<br>low = 0.7 cm; high = 6.0<br>cm<br>1 = <1.8 cm; 29.1%<br>2 = <2.8 cm; 48.0%<br>3 = <3.9 cm; 15.3%<br>4 = <4.9 cm; 4.6%<br>5 = >4.8 cm; 3.1%<br>avg. = 2.3 cm, std = 0.9 | |
| (16) PETIOLE LENGTH<br>The length of the<br>petiole from the base of<br>the petiole to the start<br>of the leaf blade at the<br>5$^{th}$, 10$^{th}$, and 15$^{th}$ node<br>pairs. | S70 = 4.1 cm for 5$^{th}$ node<br>pair; 3.3 cm for 10$^{th}$ node<br>pair; and 2.2 cm for 15$^{th}$<br>node pair<br>(Uvalde nursery, 2008)<br>Value based on an the<br>average of a minimum of<br>three plants (unit of<br>measure: cm)<br>Distribution within Sesaco<br>for 5$^{th}$ leaf based on stable<br>lines in the crossing<br>program in 2002 (Total<br>number of lines tested =<br>196 with 711 samples)<br>low = 3.0 cm; high = 17.0<br>cm<br>1 = <5.8 cm; 35.2%<br>2 = <8.6 cm; 39.8%<br>3 = <11.4 cm; 19.4%<br>4 = <14.2 cm; 4.1%<br>5 = >14.1 cm; 1.5%<br>avg. = 7.0 cm, std = 2.5<br>Distribution within Sesaco<br>for 10$^{th}$ leaf based on<br>stable lines in the crossing<br>program in 2002 (Total<br>number of lines tested =<br>196 with 711 samples)<br>low = 1.0 cm; high = 14.2<br>cm<br>1 = <3.6 cm; 53.6%<br>2 = <6.3 cm; 31.6%<br>3 = <8.9 cm; 11.7%<br>4 = <11.6 cm; 2.0%<br>5 = >11.5 cm; 1.0%<br>avg. = 4.0 cm, std = 2.1<br>Distribution within Sesaco<br>for 15$^{th}$ leaf based on<br>stable lines in the crossing<br>program in 2002 (Total<br>number of lines tested =<br>196 with 711 samples)<br>low = 0.2 cm; high = 7.4<br>cm<br>1 = <1.6 cm; 38.8% | See LEAF LENGTH (Character No. 13)<br>on how to collect leaves. In some leaves,<br>the blade on one side of the petiole starts<br>before the other side. This measure should<br>end where the earliest blade starts. There<br>are leaves that have enations where a<br>blade starts and then stops. The enations<br>are not considered part of the leaf blade<br>because they are very irregular from plant<br>to plant and within a plant and should be<br>measured as part of the petiole.<br>COMMENTS: see LEAF LENGTH<br>(Character No. 13) for effects of<br>environment |

TABLE II-continued

Characters Distinguishing the S70 Line

| Character | Rating | Methodology |
|---|---|---|
| | 2 = <3.1 cm; 41.8%<br>3 = <4.5 cm; 13.3%<br>4 = <6.0 cm; 3.1%<br>5 = >5.9 cm; 3.1%<br>avg. = 2.3 cm, std = 1.3 | |
| (17) NUMBER OF CARPELS PER CAPSULE<br>The predominant number of carpels per capsule in the middle half of the capsule zone | S70 = 2<br>(All crops, all nurseries)<br>Subjective rating based on the following values:<br>2 = bicarpellate<br>3 = tricarpellate<br>4 = quadricarpellate<br>(unit of measure: actual number<br>Distribution within Sesaco based on the introductions received in 1982-2001<br>(Total number of samples tested = 2702)<br>2 = 97.6%<br>3 = 0.0004%<br>4 = 2.3%<br>Sesaco has not developed lines with more than 2 carpels. | The rating can be taken from about 60 days after planting to all the way to the end of the crop.<br>There are many plants with mixed number of carpels as follows:<br>1. Some bicarpellate plants will have one or more nodes near the center of the capsule zone that have tri- and/or quadricarpellate capsules and vice versa.<br>2. Most tri- and quadri-carpellate plants will begin and end with bicarpellate nodes.<br>3. Some plants have only one carpel that develops. These capsules are generally bent, but on examination the 2nd carpel can be seen.<br>4. On all types, flowers may coalesce and double or triple the number of carpels.<br>5. On the seamless gene plants (gs/gs) the false membranes do not form locules. These are still considered bicarpellate. |
| (18) CAPSULE LENGTH FROM 10cap TEST<br>The length of the capsule from the bottom of the seed chamber to the top of the seed chamber from the outside of the capsule. The tip of the capsule is not included in the measurement. | S70 = 2.11 cm<br>(All experimental nurseries, 1997-2008)<br>Value based on the average of a minimum of three samples of the length taken on the median capsule in a 10 capsule sample (unit of measure: cm)<br>Distribution within Sesaco based on 10cap test in all nurseries in 1997-2002<br>(Total number of lines tested = 1,613 with 8,285 samples)<br>low = 1.3 cm; high = 4.5 cm<br>1 = <1.94 cm; 2.7%<br>2 = <2.58 cm; 67.9%<br>3 = <3.22 cm; 27.2%<br>4 = <3.86 cm; 1.9%<br>5 = >3.85 cm; 0.3%<br>avg. = 2.44 cm, std = 0.33 | After the plants are physiologically mature, take 2 capsules from five plants from the middle of the capsule zone. On three capsule per leaf axil lines, one central capsule and one axillary capsule should be taken from the same leaf axil. The measurement is taken on the median capsule of single capsule lines and on the median central capsule on three capsule lines. The measurement is taken on dry capsules because the length can shorten as much as one mm on drydown.<br>The 10 capsules can be sampled from physiological maturity through complete drydown without an effect on this character.<br>Generally, the capsules in the middle of the capsule zone are the longest on the plant.<br>COMMENTS: the length of the capsule is dependent on the amount of moisture, fertility, and population. Higher moisture and fertility increase the length. Higher population decreases the length even with adequate moisture/fertility. |
| (19) SEED WEIGHT PER CAPSULE FROM 10cap TEST<br>The weight of the seed in a capsule from the center of the capsule zone | S70 = 0.221 g<br>(All experimental nurseries, 1997-2008)<br>Value based on the average of a minimum of three samples of the weight of 10 capsules (unit of weight: grams)<br>Distribution within Sesaco based on 10cap test in all nurseries in 1997-2002<br>(Total number of lines tested = 1,613 with 8,285 samples)<br>low = 0.053 g; high = 0.476 g<br>1 = <0.138 g; 1.3%<br>2 = <0.222 g; 47.6%<br>3 = <0.307 g; 50.6%<br>4 = <0.391 g; 1.1%<br>5 = >0.390 g; 0.1%<br>avg. = 0.221 g, std = 0.039 | See CAPSULE LENGTH FROM 10CAP TEST (Character No. 18) for collection of capsules. The capsules should be dried, the seed threshed out, and the seed weighed.<br>The 10 capsules can be sampled from physiological maturity through complete drydown without an effect on this character. After drydown, only capsules with all their seed are taken. Thus, this test cannot be done on shattering lines after drydown.<br>Generally, the capsules in the middle of the capsule zone have the highest seed weight per capsule on the plant.<br>COMMENTS: see CAPSULE LENGTH FROM 10CAP TEST (Character No. 18) for the effects of environmental factors. |

TABLE II-continued

Characters Distinguishing the S70 Line

| Character | Rating | Methodology |
|---|---|---|
| (20) CAPSULE WEIGHT PER CAPSULE FROM 10cap TEST  The weight of the capsule from the center of the capsule zone after the seed has been removed | S70 = 0.133 g (All experimental nurseries,1997-2008) Value based on the average of a minimum of three samples of the weight of 10 capsules (unit of measure: grams) Distribution within Sesaco based on 10cap test in all nurseries in 1997-2002 (Total number of lines tested = 1,613 with 8,285 samples) low = 0.059 g; high— 0.395 g 1 = <0.126 g; 22.6% 2 = <0.193 g; 69.1% 3 = <0.261 g; 8.2% 4 = <0.328 g; 0.9% 5 = >0.327 g; 0.6% avg. = 0.152 g, std = 0.036 | See CAPSULE LENGTH FROM 10CAP TEST (Character No. 18) for collection of capsules. The capsules should be dried, the seed threshed out, and the capsules weighed. At times the peduncle can still be attached to the capsules. The peduncles should be removed and not weighed. The 10 capsules can be sampled from physiological maturity through complete drydown without an effect on this character. Generally, the capsules in the middle of the capsule zone have the highest capsule weight per capsule on the plant. COMMENTS: see CAPSULE LENGTH FROM 10CAP TEST (Character No. 18) for the effects of environmental factors. |
| (21) CAPSULE WEIGHT PER CM OF CAPSULE  The weight of a capsule per cm of capsule from the center of the capsule zone | S70 = 0.063 g (All experimental nurseries, 1997-2008) Value based on the average of a minimum of three samples of the weight per cm of 10 capsules (unit of measure: grams) Distribution within Sesaco based on 10cap test in all nurseries in 1997-2002 (Total number of lines tested = 1,613 with 8,285 samples) low = 0.027 g; high = 0.123 g 1 = <0.046 g; 8.2% 2 = <0.065 g; 55.5% 3 = <0.085 g; 36.5% 4 = <0.104 g; 4.4% 5 = >0.103 g; 0.5% avg. = 0.063 g, std = 0.012 | The weight is derived by dividing the CAPSULE WEIGHT PER CAPSULE FROM 10CAP TEST (Character No. 20) by the CAPSULE LENGTH FROM 10CAP TEST (Character No. 18). The 10 capsules can be sampled from physiological maturity through complete drydown without an effect on this character. COMMENTS: this character is used instead of capsule width. Capsule width is difficult to measure because there are so many variables in a capsule. In a bicarpellate capsule, the width differs when measuring across one carpel or both carpels. Capsules can also vary through the length of the capsule by being substantially narrower at the bottom, middle or top of the capsule. In 1997, four widths were measured on each capsule and then averaged. This average had a very high correlation to the capsule weight per cm of capsule. See CAPSULE LENGTH FROM 10CAP TEST (Character No. 18) for effects of environmental factors |
| (22) VISUAL SEED RETENTION  Amount of seed in most of the capsules in the middle half of the capsule zone when the plant(s) are dry enough for direct harvest with a combine | S70 = I (All crops, all nurseries) Subjective rating based on the following values: X = <50% seed retention (unsuitable for direct harvest) C = 50-74% seed retention (unsuitable for direct harvest, but may segregate V or above in future generations) V = >74% seed retention (sufficient seed retention for 10cap testing) W = >74% seed retention on weathering in field after rains and/or winds I = in using the "drum test" the seed in the capsules do not rattle and >85% of the capsules on the plant(s) harvested have visible seed in the tips of the capsules four or more weeks after the ideal harvest time. The "I" rating is used for all of the | This rating is used for plants that are being selected for advanced testing whether individually or in a bulk with all the plants having the same level of seed retention. Most "X" plants can be identified from the first capsule that dries since the seed will begin falling out immediately. A "C" (close to V) plant will have some capsules with seed and some without. A "V" (visual shatter resistance) plant can be identified when the first 50% of the capsules have dried, but a "V+" rating should not be used until the complete plant is dry and most of the capsules are showing seed retention. Some "V" plants can be upgraded to "W" after the dry capsules have been subjected to weather (rain and/or wind). "V" and "W" become non-dehiscent only after 10cap testing with about an 80% passing rate. 10cap testing is done on "I" selections have had about a 90% passing rate. The "drum test" consists of placing the fingers from one hand about ½ inch from the center of the main stem and then striking the stem alternately with one finger |

TABLE II-continued

Characters Distinguishing the S70 Line

| Character | Rating | Methodology |
|---|---|---|
| | capsules on the plant. '+' and '−' modifiers can be used for the X, C, V, W, and I. | and then the other finger in rapid succession. The human ear can perceive degree of rattling over a range. IND is defined as having no rattle. Degree of rattle in this test correlates with loss of increasing amounts of seed as capsules are exposed to weather conditions. COMMENTS: the ratings above should be made under normal conditions (600 mm of annual rainfall and 30 kg/ha of nitrogen) through high moisture/fertility conditions. In drought or very low fertility conditions, it has been observed that there is less seed retention. In addition, high populations may lead to low moisture or fertility causing less seed retention. If unusual environmental conditions are present, the effects should be taken into consideration prior to rating. |
| (23) SHAKER SHATTER RESISTANCE FROM 10cap TEST The amount of seed retention after the capsules are dry and put through a shaker (10 capsule sample) | S70 = 77.4 % (All experimental nurseries, 1997-2008) Value based on the average of a minimum of three samples of the percentage of seed retained in 10 capsules (unit of measure: Actual Number expressed as percentage) Distribution within Sesaco based on 10cap test in all nurseries in 1997-2002 (Total number of lines tested = 1,613 with 8,285 samples) low = 0; high = 100 1 = <20; 12.9% 2 = <40; 6.9% 3 = <60; 23.4% 4 = <80; 47.7% 5 = >79.9; 9.2% avg. = 55.9%, std = 23.9 | See CAPSULE LENGTH FROM 10CAP TEST (Character No. 18) for collection of capsules. The capsules should be dried. The capsules and any seed that has fallen out should then be placed in flasks on a reciprocal shaker with a 3.8 cm stroke with 250 strokes/min for 10 minutes (see U.S. Pat. No. 6,100,452). The seed that comes out of the capsules should be weighed as 'out seed.' The retained seed should be threshed out of the capsules and weighed to compute the 'total seed. The shaker shatter resistance is computed as a percentage as follows: (total seed— out seed)/total seed. The 10 capsules can be sampled from physiological maturity through complete drydown without an effect on this character for shatter resistant types. When taking capsules after drydown, only capsules with all their seed are taken. Thus, this test cannot be done on shattering lines after drydown. COMMENTS: The ratings above should be made under normal conditions through high moisture/fertility conditions. In drought or very low fertility conditions, it has been observed that there is less seed retention. In additions, high populations may lead to low moisture or fertility causing there is less seed retention. If unusual environmental conditions are present, the effects should be taken into consideration prior to rating. Lines with shaker shatter resistance >64.9% are known as non-dehiscent lines (see U.S. Pat. No. 6,100,452). |
| (24) CAPSULE SHATTERING TYPE Character Amount of seed retention in a line or plant | S70 = SR (All crops, all nurseries) Rating Subjective rating based on the following values: SUS = Super-shattering (<25%) SHA = Shattering (<50%) SSH = Semi-shattering (50 to 75%; a rating of C) SR = Shatter resistant (>75%; a rating of V, W, or I) ID = Indehiscent (presence of id/id with capsule closed) IDO = Indehiscent (presence of id/id with capsule open at tip) | The rating is based on visual observations as to seed retention as the Methodology plants remain standing in the field without shocking. SUS, SHA, SSH, SR, ID, and GS are terms used by international sesame breeders and can be correlated to the Sesaco definitions used by Sesaco by VISUAL SEED RETENTION (Character No. 22). GS plants can be identified while the plant is putting on capsules or at drydown because the carpels in the capsules do not form false membranes. There are plants that will have capsules with false membranes on the lower and upper nodes but most of the capsules show no false membranes. |

TABLE II-continued

Characters Distinguishing the S70 Line

| Character | Rating | Methodology |
|---|---|---|
| | GS = Seamless (presence of gs/gs with capsule closed) GSO = Seamless (presence of gs/gs with capsule open at tip) | ID plants can be identified during the growing season in that they have enations on the bottoms of the leaves. At dry down they are more difficult to distinguish from other lines that have closed capsules (other than GS). There is less of a suture than other capsule types. COMMENTS: Most environmental factors do not have much of an effect on capsule shattering type other than to make it more difficult to distinguish in the overlap zone. Generally, higher moisture, higher fertility, and lower populations will decrease the shattering a small amount— less than 10%. The wind can have a large effect in decreasing the amount of seed retention. Rain, dew and fog can also reduce seed retention. |
| (25) NON-DEHISCENT TEST A line that has passed Character the non-dehiscent test of having shaker shatter resistance >64.9% is considered an ND line in accordance with U.S. Pat. No. 6,100,452. | S70 = ND (All crops, all nurseries) Rating Subjective rating based on the following values: ND = Non-dehiscent line XX = Line that does not pass the non-dehiscent test ND distribution within Sesaco based on 10cap test in all nurseries in 1997-2007 (Total number of samples tested = 10,905) ND = 53.6% XX = 46.4% | Lines are designated as ND only after they have undergone a minimum of 3 shaker shatter resistance tests. In order to be Methodology considered an ND variety, the line must pass the ND threshold in multiple nurseries for multiple years. |
| (26) IMPROVED NON-DEHISCENT VISUAL RATING (IND) Amount of seed in most of the capsules in the plants in a plot four or more weeks after the ideal harvest time. | S70 = 7.5 (Uvalde nursery, 2008) S70 = 7.4 (Lorenzo nursery, 2008) Value based on the average on a minimum of three plots of a subjective rating based on the percentage of capsules with visible seed retention 8 < 100% 7 < 85% 6 < 70% 5 > 55% Z < 55% '*', '+' and '−' modifiers can be used. For averages, 0.5 is added for '*', 0.33 is added for a '+' and 0.33 is subtracted for a '−', e.g., "7+" = 7.33. IND distribution as an average of nurseries in Uvalde and Lorenzo from 2006-2008. (Total number of lines tested = 288 with 801 samples in 2006) low = 2.97; high = 7.33 1 = <6.0; 2.1% 2 = <6.5; 20.8% 3 = <7.0; 13.2% 4 = <7.5; 63.9% 5 = >7.5; 0% avg. = 6.77, std = 0.54 Note: The percentage of lines between 7.0 and 7.6 is very high because Sesaco only uses these ratings to evaluate lines | This rating is used for a plot or field that is being evaluated. The data is taken four or more weeks after the ideal harvest time. See DAYS TO DIRECT HARVEST (Character No. 31). Estimate the percentage of capsules that have visible seed at the top. In the beginning in order to develop an eye for the rating, the evaluator should observe all of the capsules and rate each of them; get a counts of those with no visible seeds and a count of total capsules; and compute a percentage. Once the evaluator is skilled, there is no need to count the capsules. There is a very high correlation between this rating upon visual evaluation and the amount of rattling generated by the "drum test" defined above in VISUAL SHATTER RESISTANCE (Character No. 22). Although retention can vary from plant to plant and even within a plant, the overall rating is correlatable with IND. In crossing between lines, in early generations there is a segregation of IND plants and non-IND plants. In this case the plot is given a rating of the majority of plants while the plants selected can have a higher rating which is reflected in VISUAL SEED RETENTION. The ratings that are cited in this character are for plots, but a ratings of 7 or 8 are only given if over 90% of the plants have the higher rating. |

TABLE II-continued

Characters Distinguishing the S70 Line

| Character | Rating | Methodology |
|---|---|---|
| (27) IMPROVED NON-DEHISCENCE TEST An ND line that passes the drum test and has a visual IND rating >6.99 is considered IND. A method for traditional breeding of an IND line is described in concurrently filed U.S. patent application Ser. No. 12/041,257. ND and IND lines should not have id or gs alleles. | that are released varieties, IND lines, or lines segregating IND. S70 = IND (All crops, all nurseries Subjective rating based on the following values: IND = Improved Non-dehiscent line ZZ = Line that does not pass the impoved non-dehiscent test Distribution within Sesaco based on visual IND (Total number of lines tested = 1,934 in all nurseries from 2005 to 2007) IND = 9.5% ZZ = 90.5% | Varieties were designated as IND after they demonstrated the defined characteristics with statistically significant data. |
| (28) DAYS TO FLOWERING Number of days from planting until 50% of the plants are flowering | S70 = 38 days Rating (Uvalde nursery, 2008) Value based on the average of a minimum of three plots of the number of days (unit of measure: days) Distribution within Sesaco based on lines in Uvalde nursery in 2000-2001 (Total number of samples tested = 1,831) low = 33 days; high = 89 days 1 = <44.2 days; 87.9% 2 = <55.4 days; 7.8% 3 = <66.6 days; 2.4% 4 = <77.8 days; 1.7% 5 = >77.7 days; 0.2% avg. = 40.9 days, std = 6.3 | The vegetative phase in sesame is from the time of planting to the start of flowering. This data is taken as a date and later converted to number of days. Flowering is defined as flowers that are open—not buds. COMMENTS: flowering can be accelerated by drought and it can be delayed by higher moisture and/or fertility. Higher heat units will decrease the days to flowering. Some lines are photosensitive and will only begin flowering at a certain number of hours of daylight. Start of flowering does not always equate to start of capsule formation. Many lines will flower and not set capsules from the first flowers. |
| (29) DAYS TO FLOWER TERMINATION Number of days from planting until 90% of the plants have stopped flowering | S70 = 74 days (Uvalde nursery, 2008) Value based on the average of a minimum of three plots of the number of days (unit of measure: days) Distribution within Sesaco based on lines in Uvalde nursery in 2000-2001 (Total number of samples tested = 2,668) low = 61 days; high = 114 days 1 = <71.6 days; 21.1% 2 = <82.2 days; 61.5% 3 = <92.8 days; 15.9% 4 = <103.4 days; 0.8% 5 = >103.3 days; 0.8% avg. = 77.1 days, std = 6.9 | The reproductive phase of sesame is from the start to the end of flowering. This data is taken as a date and later converted to number of days. Flowering is defined as flowers that are open—not buds. At the end of the flowering period, the rate that a plant puts on open flowers is reduced. Thus, there can be more than 10% of plants with buds and still have reached this measure since there will not be more than 10% with open flowers on any one day. The measure is based on the number of plants and not the number of flowering heads. The branches will stop flowering before the main stem, and thus the plot will appear like there are more plants not flowering. COMMENTS: flower termination can be accelerated by lower moisture and/or fertility, and it can be delayed by higher moisture and/or fertility. Higher heat units will decrease the DAYS TO FLOWER TERMINATION. It is known that there are lines that stop flowering sooner than expected in northern latitudes, but it is not known if this is due to shorter photoperiod or cool temperatures. |
| (30) DAYS TO PHYSIOLOGICAL MATURITY Number of days from planting until 50% of the plants reach physiological maturity | S70 = 98 days (Uvalde nursery, 2008) Value based on the average of a minimum of three plots of the number of days (unit of measure: days) | The ripening phase of sesame is from the end of flowering until physiological maturity. This data is taken as a date and later converted to number of days. Physiological maturity (PM) is defined as the point at which ¾ of the capsules have seed with |

TABLE II-continued

Characters Distinguishing the S70 Line

| Character | Rating | Methodology |
|---|---|---|
| | Distribution within Sesaco based on lines in Uvalde nursery in 2000-2001 (Total number of samples tested = 2,374) low = 77 days; high = 140 days<br>1 = <89.6 days; 16.8%<br>2 = 102.2 days; 58.0%<br>3 = <114.8 days; 23.6%<br>4 = <127.4 days; 1.4%<br>5 = >127.3 days; 0.2%<br>avg. = 97.1 days, std = 7.1 | final color. In most lines, the seed will also have a seed line and tip that is dark. COMMENTS: The concept of C physiological maturity in sesame was developed by M. L. Kinman (personal communication) based on the concept of determining the optimum time to cut a plant and still harvest 95-99% of the potential yield. The Kinman ratings were used for sesame in the 1950-60s when the plants were cut while still green and manually shocked to dry. When the seed has final color, the seed can germinate under the proper conditions. If the plant is cut at physiological maturity, most of the seed above the ¾ mark will go to final color and are mature enough to germinate, but will not have as much seed weight. Since in even a fully mature plant, there is less seed weight made at the top of the plant, this loss of seed weight does not seriously affect the potential seed weight of the plant. Although present harvest methods let the plants mature and go to complete drydown, PM is important because after that point, the crop is less susceptible to yield loss due to frost or disease. The PM is also important if the crop is to be swathed or harvest aids are to be applied. Physiological maturity can be accelerated by lower moisture and/or fertility, and it can be delayed by higher moisture and/or fertility. Higher heat units will decrease the days to physiological maturity. Cool weather can delay physiological maturity. |
| (31) DAYS TO DIRECT HARVEST Number of days from planting until there is enough drydown for direct harvest | S70 = 141 days (Uvalde nursery, 2008) Value based on the average of a minimum of three plots of the number of days (unit of measure: days) Distribution within Sesaco based on lines in all nurseries from 2004 tthrough 2006 (Total number of samples tested = 1,998) low = 103 days; high = 161 days<br>1 = <114.6 days; 3.3%<br>2 = <126.2 days; 13.3%<br>3 =<br>4 =<br>5 =<br>avg. = 136.7 days, std = 10.3 | The drying phase of sesame is from physiological maturity until direct harvest. This data is taken as a date and later converted to number of days. Direct harvest is defined as the date at which the plants are dry enough for combining seed at 6% or less moisture. Over 99% of the sesame in the world is cut by hand before the plant completely dries down, and the plants are manually shocked to dry down. The plants should be dry below where the cutter bar of the combine will hit the plants. In many lines, 15-20 cm from the ground can be green without an effect on the moisture of the seed. In taking the data on a plot, the plants at the aisle have more moisture and fertility available and will dry down later. The same is true for plants within the plot that have a gap of half a meter between plants. These plants should be disregarded in taking the data. In addition, there are few farmer fields that dry down uniformly because of varying soils and moisture. There is a certain amount of green that can be combined and still attain the proper moisture. The amount of green allowable is also dependent on the humidity at the day of combining—the lower the humidity the higher the amount of allowable green. COMMENTS: This date is the most variable number of days that define the phenology of sesame because weather is so important. In dry years with little rainfall, the plants will run out of moisture sooner and will dry down faster than in years with more rainfall. Fields that are irrigated by pivots will generally dry down |

TABLE II-continued

Characters Distinguishing the S70 Line

| Character | Rating | Methodology |
|---|---|---|
| | | faster than fields with flood or furrow irrigation because pivots do not provide deep moisture. Fields with less fertility will drydown faster than fields with high fertility. Fields with high populations will dry down faster than fields with low populations. In low moisture situations lines with a strong taproot will dry down later than lines with mostly shallow fibrous roots. |
| (32) LODGING RESISTANCE The amount of lodging | S70 = 7.3 (Uvalde nursery 2007); S70 = 8.0 (Lorenzo nursery 2007) Average of a minimum of three plots of a subjective rating based on the following values: 0 to 8 rating 8 = no lodging 7 = Less than 5% of plants lodged 4 = 50 % of plants lodged 1 = All plants lodged Intermediate values are used. Distribution within Sesaco based on lines in Uvalde and Lorenzo nurseries in 2007 (Total number of samples tested = 1061) low = 1.0; high = 8.0 1 = <2.4; 3.1 0/0 2 = <3.8; 6.9% 3 = <5.2; 22.6% 4 = <6.6; 18.9% 5 = >8.0; 48.4% avg. = 6.1, std = 1.7 | The data is taken after physiological maturity (see DAYS TO PHYSIOLOGICAL MATURITY—Character No. 30) and before direct harvest (see DAYS TO DIRECT HARVEST—Character No. 31). Lodging that occurs after direct harvest in nurseries would not be a factor in commercial sesame. There are three types of lodging: where the plants break at the stem, where the plants bend over but do not break, and where the plants uproot and bend over. When a plant breaks over, it will rarely produce any new seed, and the existing seed may or may not mature. If there is a total break, there is no hope, but if there is still some active stem translocation through the break, there can be some yield recovery. The main causes for uprooting of plants are shallow root systems and fields that have just been irrigated, creating a soft layer of soil. When a plant bends over early in development, some lines adapt better than others in terms of having the main stems turn up and continue flowering. The tips of the branches are usually matted under the canopy and will rarely turn up, but new branches can develop. As the plants go to drydown and the weight of the moisture is lost, many of the bent plants will straighten up making the crop easier to combine. COMMENTS: The major cause of lodging is the wind. In areas where there are constant winds such as in Oklahoma and northern Texas, the plants adjust by adding more lignins to the stems, and it takes a stronger wind to cause lodging than in areas such as Uvalde where there normally only breezes unless there is a strong front or thunderstorm that passes through. In areas with more root rots, the stems are weak and it takes little wind to lodge the plants. |
| (33) SEED COLOR The color of the seed coat | S70 = BF (All crops, all nurseries) Subjective rating based on the following values: WH = White BF = Buff TN = Tan LBR = Light brown GO = Gold LGR = Light gray GR = Gray BR = Brown RBR = Reddish brown BLK = Black Distribution within Sesaco based on seed harvested in all nurseries in 1982- 2001 (Total number of samples tested = 161,809) WH = 0.8% BF = 74.8% TN = 9.0% LBR = 1.4% | This data is taken in the laboratory with the same lighting for all samples. The seed from the whole plant is used. Seed coat color is taken on mature seeds. If there is any abnormal termination, the colors are not quite as even. The color of immature seed varies. Usually light seeded lines have tan to light brown immature seed; tan, light brown, gold, brown light gray, and gray lines have lighter immature seed; black lines can have tan, brown, or gray immature seed. Usually, moisture, fertility, population and light intensity do not have an effect on seed coat color. Light colored seeds in a drought may have a yellowish tinge. Seeds in some lines in the tan, light brown and gold range can change from year to year among themselves. |

TABLE II-continued

Characters Distinguishing the S70 Line

| Character | Rating | Methodology |
|---|---|---|
| | GO = 1.5%<br>LGR = 0.6%<br>GR = 1.4%<br>BR = 6.5%<br>RBR = 0.6%<br>BLK = 3.5% | |
| (34) SEED WEIGHT—100 SEEDS FROM 10cap TEST<br>Weight of 100 seeds taken from the 10cap tests which are taken from the middle of the plant. | S70 = 0.326 g<br>(All experimental nurseries, 1997-2008)<br>Value based on the average of a minimum of three samples of the weight of 100 seeds from the 10 capsules (unit of weight: grams)<br>Distribution within Sesaco based on stable lines in all nurseries in 1997-2002 (Total number of lines tested = 820 with 2,899 samples)<br>low = 0.200 g; high = 0.455 g<br>1 = <0..251 g; 10.1%<br>2 = <0.302 g; 48.4%<br>3 = <0.353 g; 34.0%<br>4 = <0.404 g; 7.2%<br>5 = >0.403 g; 0.2%<br>avg. = 0.298 g, std = 0.04 | See CAPSULE LENGTH FROM 10CAP TEST (Character No. 18) for collection of capsules.<br>Count out 100 seeds and weigh. The seed must be dry.<br>COMMENTS: the weight increases with higher moisture/fertility. Generally, the weight of the seed from the whole plant is lighter than the seed weight taken from the 10cap test. |
| (35) COMPOSITE KILL RESISTANCE<br>The amount of plants killed by root rots in the Sesaco nurseries | S70 = 7.2<br>(Uvalde nursery, 2007);<br>Average of a minimum of three plots of a subjective rating based on the following values: Ratings are based on the number of plants killed in a plot.<br>Before physiological maturity (PM), the following ratings are used:<br>1 = >90% kill before DAYS TO FLOWERING TERMINATION (Character No. 29)<br>2 = >90% kill between DAYS TO FLOWERING TERMINATION (Character No. 29) and DAYS TO PHYSIOLOGICAL MATURITY (Character No. 30)<br>After PM, the following ratings are used:<br>3 = >90% kill<br>4 = 50 to 89% kill<br>5 = 25 to 49% kill<br>6 = 10 to 24% kill<br>7 = less than 10% kill<br>8 = no kill<br>Distribution within Sesaco based on lines in Uvalde nursery in 2000-2001 (Total number of samples tested = 3045)<br>low = 1.00; high = 8.00<br>1 = <1.6; 1.7%<br>2 = <3.2; 16.7%<br>3 = <4.8; 38.7%<br>4 = <6.4; 31.2%<br>5 = >6.3; 11.6%<br>avg. = 4.52, std = 1.49 | On the week a plot reaches PM, a rating is assigned. The ratings are then taken for 2 additional weeks. The three ratings are averaged for a final kill rating. For example, if a plot has a final kill of 766, the average for the plot will be 6.33. When a value of 1 or 2 is assigned, there are no additional ratings, and there is no averaging.<br>There are three root diseases that affect sesame in Texas: *Fusarium oxysporum*, *Macrophomina phaseoli*, and *Phytophtora parasitica*. Between 1988 and the present, spores of these three have been accumulated in one small area (1 square km) north of Uvalde, and thus it is an excellent screening area for the diseases. Although each root rot attacks sesame in a different way with different symptoms, no effort is made to differentiate which disease is the culprit in each plot. Pathological screenings in the past have found all 3 pathogens present in dead plants.<br>COMMENTS: normally if decreasing, the ratings will decrease a maximum of one value per week. There is an overlap between any two ratings, but this is overcome to a certain extent by using three ratings over 2 weeks.<br>The amount of kill is usually increased with any type of stress to the plants. Drought can increase the amount of *Macrophomina*; too much water can increase the amount of *Phytophtora*; high temperatures and humidity can increase the amount of *Fusarium* and *Phytophtora*. High population can increase all three diseases.<br>The ratings for any one year can be used to compare lines grown in that year, but should not be used to compare lines grown in different years. The amount of disease in any one year is highly dependent on moisture, humidity, and temperatures. |

TABLE II-continued

Characters Distinguishing the S70 Line

| Character | Rating | Methodology |
|---|---|---|
| (36) RESISTANCE TO FUSARIUM WILT (*F. oxysporum*) Amount of resistance to Fusarium wilt | S70 = NT Average of a minimum of three plots of a subjective rating based on the following values: 0 to 8 scale of the % of infected plants 8 = Zero disease 7 = <10% infected 4 = 50% infected 1 = >90% infected 0 = all infected Intermediate values are used. NT = not tested NEC = no economic damage—not enough disease to do ratings | Ratings can be done in several ways: 1. Take ratings after the disease is no longer increasing 2. Take ratings on consecutive weeks until disease is no longer increasing and average ratings. 3. Take periodic ratings and average ratings. COMMENTS: *Fusarium* has been a problem in South Texas, particularly on fields that have been planted with sesame before. Normally, only the COMPOSITE KILL RESISTANCE (Character No. 35) rating is taken. |
| (37) RESISTANCE TO PHYTOPHTORA STEM ROT (*P. parasitica*) Amount of resistance to *Phytophtora* stem rot | S70 = NT Subjective rating See Values for *Fusarium* | See Methodology for RESISTANCE TO FUSARIUM WILT (Character No. 36) COMMENTS: *Phytophtora* has been a problem in Arizona and Texas, particularly on fields that have been over-irrigated. Normally, only the COMPOSITE KILL RESISTANCE (Character No. 35) rating is taken. |
| (38) RESISTANCE TO CHARCOAL ROT (*Macrophomina phaseoli*) Amount of resistance to Charcoal rot | S70 = NT Subjective rating COMMENTS: *Macrophomina* has been See Values for *Fusarium* | See Methodology for RESISTANCE TO FUSARIUM WILT (Character No. 36) a problem in Arizona and Texas, particularly on fields that go into a drought. Normally, only the COMPOSITE KILL RESISTANCE (Character No. 35) rating is taken. |
| (39) RESISTANCE TO BACTERIAL BLACK ROT (*Pseudomonas sesame*) Amount of resistance to bacterial black rot | S70 = NT Average of a minimum of three plots of a subjective rating based on the following values: 0 to 8 scale of the % of infected plants 8 = Zero disease 7 = <10% infected 4 = 50% infected 1 = >90% infected 0 = all infected Intermediate values are used. NT = not tested NEC = no economic damage—not enough disease to do ratings Distribution within Sesaco based on lines in Uvalde nursery in 2004 (Total number of samples tested = 593) low = 4.00; high = 8.00 1 = <2.4; 0.0% 2 = <3.8; 0.0% 3 = <5.2; 8.6% 4 = <6.6; 16.0% 5 = >6.5; 75.4% avg. = 7.13, std = 1.00 | See Methodology for RESISTANCE TO FUSARIUM WILT (Character No. 36) COMMENTS: this disease occurs occasionally when there is continual rainy weather with few clouds. In most years, the disease abates once the weather changes. No economic damage has been noticed. |
| (40) RESISTANCE TO SILVERLEAF WHITEFLY (*Bemisia argentifolii*) Amount of resistance to the silverleaf whitefly | S70 = NEC (Uvalde nursery, 2007) There were a few insects on S70, but not enough to rate S70 or the other lines. Average of a minimum of three plots of a subjective rating based on the following values: 0 to 8 scale of the % of infected plants 0 to 8 scale | Ratings can be done in several ways: 1. Take ratings after the insects are no longer increasing. 2. Take ratings on consecutive weeks until insects are no longer increasing and average ratings. 3. Take periodic ratings and average ratings. COMMENTS: there have been very few years (1991-1995) where the incidence of silverleaf whitefly has affected nurseries or commercial crops. In most |

TABLE II-continued

Characters Distinguishing the S70 Line

| Character | Rating | Methodology |
|---|---|---|
| | 8 = Zero insects<br>7 = Few insects<br>4 = Many insects<br>1 = Insects killing the plants<br>Intermediate values are used.<br>NT = not tested<br>NEC = no economic damage—not enough insects to do ratings | years, a few whiteflies can be seen in the sesame with no economic damage. In the middle 1990s, the USDA began introducing natural predators of the silverleaf whitefly in the Uvalde area. It is not known if the predators reduced the effects of the whitefly or there is a natural tolerance to whitefly in the current varieties. Higher temperatures decrease the number of days between generations. There are indications that higher moisture and fertility increase the incidence of white flies, but there is no definitive data. The sweet potato whitefly (*Bemisia tabaci*) has been observed in nurseries since 1978 without any economic damage. |
| (41) RESISTANCE TO GREEN PEACH APHIDS (*Myzus persicae*)<br>Amount of resistance to the green peach aphid | S70 = NT<br>(Uvalde nursery, 2004)<br>Subjective rating; see Values for Whitefly<br>Distribution within Sesaco based on lines in Uvalde nursery in 2004<br>(Total number of samples tested = 412)<br>low = 1.00; high = 8.00<br>1 = <2.4; 1.0%<br>2 = <3.8; 0.5%<br>3 = <5.2; 10.7%<br>4 = <6.6; 4.8%<br>5 = >6.5; 83.0%<br>avg. = 7.04, std = 1.35 | See Methodology for RESISTANCE TO SILVERLEAF WHITEFLY (Character No. 40)<br>COMMENTS: there have been very few years (1990-1995) where the incidence of green peach aphid has affected nurseries or commercial crops. In most years, a few aphids can be seen in the sesame with no economic damage. There have been many years in West Texas when the cotton aphid has decimated the cotton and did not build up on adjacent sesame fields. Higher moisture and fertility increase the susceptibility to aphids. |
| (42) RESISTANCE TO POD BORERS (*Heliothis* spp.)<br>Amount of resistance to pod borers | S70 = NT<br>Subjective rating; see Values for Whitefly | See Methodology for RESISTANCE TO SILVERLEAF WHITEFLY (Character No. 40)<br>COMMENTS: there have been very few years (1985) where the incidence of *Heliothis* has affected nurseries or commercial crops. In most years, a few borers can be seen in the sesame with no economic damage. |
| (43) RESISTANCE TO ARMY WORMS (*Spodoptera* spp.)<br>Amount of resistance to army worms | S70 = NT<br>Subjective rating; see Values for Whitefly | See Methodology for RESISTANCE TO SILVERLEAF WHITEFLY (Character No. 40)<br>COMMENTS: there have been very few years (1984-1987) where the incidence of *Spodoptera* has affected commercial crops in Arizona. In Texas, army worms have decimated cotton and alfalfa fields next to sesame without any damage to the sesame. It is not known if the Arizona army worm is different from the Texas army worm. |
| (44) RESISTANCE TO CABBAGE LOOPERS (*Pieris rapae*)<br>Amount of resistance to cabbage loopers | S70 = NEC<br>( Lorenzo nursery 2007)<br>Subjective rating; see values for Whitefly | See Methodology for RESISTANCE TO SILVERLEAF WHITEFLY (Character No. 40)<br>COMMENTS: there have been very few years (1992-1993) where the incidence of cabbage loopers has affected nurseries. In commercial sesame, cabbage loopers have been observed with no economic damage. |

[a] Uvalde nursery planted north of Uvalde, Texas (latitude 29°22' north, longitude 99°47' west, 226 m elev) in middle to late May to early June from 1988 to the present; mean rainfall is 608 mm annually with a mean of 253 mm during the growing season; temperatures range from an average low of 3° C. and an average high of 17° C. in January to an average low of 22° C. and an average high of 37° C. in July. The nursery was planted on 96 cm beds from 1988 to 1997 and on 76 cm beds from 1998 to the present. The nursery was pre-irrigated and has had 2-3 post-plant irrigations depending on rainfall. The fertility has varied from 30-60 units of nitrogen.

[b] Lorenzo nursery planted southeast of Lubbock, Texas (latitude 33°40' north, longitude 101°49' west, 1000 m elev) in mid June from 2004 to the present; mean rainfall is 483 mm annually with a mean of 320 mm during the growing season; temperatures range from an average low of −4° C. and an average high of 11° C. in January to an average low of 20° C. and an average high of 33° C. in July. The nursery was planted on 101 cm beds. The nursery was rainfed. The fertility was 30 units of nitrogen.

In developing sesame varieties for the United States, there are seven characters that are desirable for successful crops: SHAKER SHATTER RESISTANCE (Character No. 23), IMPROVED NON-DEHISCENT VISUAL RATING (Character No. 26), COMPOSITE KILL RESISTANCE (Character No. 35), DAYS TO PHYSIOLOGICAL MATURITY (Character No. 30), YIELD AT DRYDOWN (Character 11), SEED COLOR (Character No. 33), and SEED WEIGHT—100 SEEDS FROM 10CAP TEST (Character No. 34). The first four characters contribute to YIELD AT DRYDOWN which is the most important economic factor normally considered by a farmer in the selection of a variety. The last two characters determine the market value of the seed.

SHAKER SHATTER RESISTANCE and IMPROVED NON-DEHISCENT VISUAL RATING determine how well the plants will retain the seed while they are drying down in adverse weather.

COMPOSITE KILL RESISTANCE determines whether the plants can finish their cycle and have the optimum seed fill.

DAYS TO PHYSIOLOGICAL MATURITY determines how far north and to which elevation the varieties can be grown.

In improving the characters, the YIELD AT DRYDOWN has to be comparable to or better than current varieties, or provide a beneficial improvement for a particular geographical or market niche.

In the United States and Europe, the SEED COLOR is important since over 95% of the market requires white or buff seed. There are limited markets for gold and black seed in the Far East. All other colors can only be used in the oil market.

SEED WEIGHT—100 SEEDS FROM 10CAP TEST determines the market for the seed. Lack of COMPOSITE KILL RESISTANCE can reduce SEED WEIGHT—100 SEEDS FROM 10CAP TEST. In parts of the United States where there is little rain in dry years, the lack of moisture can reduce the SEED WEIGHT—100 SEEDS FROM 10CAP TEST.

There are other characters important in developing commercial sesame varieties explained in Langham, D. R. and T. Wiemers, 2002. "Progress in mechanizing sesame in the US through breeding", In: J. Janick and A. Whipkey (ed.), *Trends in new crops and new uses*, ASHS Press, Alexandria, Va. BRANCHING STYLE (Character No. 1), HEIGHT OF PLANT (Character No. 5), HEIGHT OF FIRST CAPSULE (Character No. 6), and PRESENCE OF PYGMY GENE (Character No. 10) are important in combining. CAPSULE ZONE LENGTH (Character No. 7), NUMBER OF CAPSULE NODE PAIRS (Character No. 8), AVERAGE INTERNODE LENGTH WITHIN CAPSULE ZONE (Character No. 9), and SEED WEIGHT PER CAPSULE (Character No. 19) are important in creating potential YIELD AT DRYDOWN (Character No. 11). LEAF DIMENSIONS (Characters No. 13, 14, 15, and 16) are important in determining optimum populations.

NUMBER OF CAPSULES PER LEAF AXIL (Character No. 2), NUMBER OF CARPELS PER CAPSULE (Character No. 17), CAPSULE LENGTH (Character No. 18), CAPSULE WEIGHT PER CAPSULE (Character No. 20), and CAPSULE WEIGHT PER CM OF CAPSULE (Character No. 21) are important in breeding for VISUAL SEED RETENTION (Character No. 22) and IMPROVED NON-DEHISCENT VISUAL RATING (Character No. 26) which lead to testing for SHAKER SHATTER RESISTANCE (Character No. 23) and determining the CAPSULE SHATTERING TYPE (Character No. 24), NON-DEHISCENT TEST (Character 25) and IMPROVED NON-DEHISCENT TEST (Character No. 27).

DAYS TO FLOWERING (Character No. 28), DAYS TO FLOWER TERMINATION (Character No. 29), DAYS TO PHYSIOLOGICAL MATURITY (Character No. 30), and MATURITY CLASS (Character No. 3) are highly correlated and important in determining the phenology and geographical range for the variety.

DAYS TO DIRECT HARVEST (Character No. 31) is important in that once the plants reach physiological maturity there is no weather event that will increase yield and many weather events that may substantially lower the yield. A shorter drying phase increases yield. PLANT PHENOTYPE (Character No. 4) is a summary character of characters 1, 2, and 3 that allows an overall visualization of the line.

RESISTANCE TO DROUGHT (Character No. 12) becomes important in reducing yield and seed weight. Even though there was a drought in the growing areas in 2006 and 2008, there has not been a drought in nurseries planted since 2000 because of irrigation. LODGING RESISTANCE (Character No. 32) is important in years when there are high winds in the growing areas. The resistance characters (Characters No. 36, 37, 38, 39, 40, 41, 42, 43, and 44) are important in reducing the losses from diseases and pests.

Over the past 32 years, Sesaco has tested over 3,000 introductions from all over the world. Commercial samples have been obtained from China, India, Sudan, Ethiopia, Burkina Faso, Nigeria, Mozambique, Pakistan, Myanmar, Bangladesh, Vietnam, Egypt, Mexico, Guatemala, Nicaragua, Venezuela, Thailand, Turkey, Upper Volta, Uganda, Mali, Kenya, Indonesia, Sri Lanka, Afghanistan, Philippines, Colombia, Ivory Coast, Gambia, Somalia, Eritrea, Paraguay, Bolivia, and El Salvador. Additional research seed has been received from the commercial countries and from many other countries such as Australia, Iraq, Iran, Japan, Russia, Jordan, Yemen, Syria, Morocco, Saudi Arabia, Angola, Argentina, Peru, Brazil, Cambodia, Laos, Sri Lanka, Ghana, Gabon, Greece, Italy, South Korea, Libya, Nepal, Zaire, England and Tanzania. Research seed received from one country may have originated from another unspecified country. All of the commercial and research introductions have CAPSULE SHATTERING TYPE (Character No. 24) of shattering, "SHA".

Using selected characters from Table II, Table III provides a character differentiation between S70 and name cultivars from all over the world.

TABLE III

Character Differentiation of Various Sesame Varieties [a]

| Character | Rating | Name cultivars tested by Sesaco |
|---|---|---|
| CAPSULE SHATTERING TYPE (Character No. 24) | SHA | Eliminate the following from the world: From Venezuela: Venezuela 51, Venezuela 52, Guacara, Aceitera, Inamar, Acarigua, Morada, Capsula Larga, Arawaca, Piritu, Glauca, Turen, DV9, Fonucla, UCLA From Mexico: Pachequeno, Yori, Anna, Teras, Denisse, Canasta, Tehvantepeter From India: TMV1, TMV3 From Turkey: Ozberk, Muganli, Gamdibi, Marmara From Israel: DT45 From Guatemala: R198, R30 From Paraguay: Escoba and INIA. From Texas: Llano, Margo, Dulce, Blanco, Paloma, Oro, Renner 1 and 2, Early Russian From California: UCR3, UCR4, Eva, Calinda (Cal Beauty) From Thailand: KU18 From Korea: Danback, Gwansan, Pungyiong, Suweon, Yuseong, Hanseon, Ahnsan, Kwangsan, Jinback, Pungsan, Sodan, Yangheuk, Konheuk, Whaheuck, Sungboon |
| | SSH | Eliminate from Sesaco: S02, S03, S04, S05, S06, S07, S08, S09, S10, S12, S14 |
| | ID | Eliminate the following from the world: From Venezuela: G2, Morada id From Texas: Rio, Delco, Baco, Improved Baco, Roy, Eli From South Carolina: Palmetto From California: UCR234 From Sesaco: S01 |
| | SR | All others, go to NON-DEHISCENT TEST |
| NON-DEHISCENT TEST (Character No. 25) | XX | Eliminate from Sesaco: S11, S15, S16, S17, S18, S19, S20, S21 |
| | ND | All others to the Improved NON-DEHISCENT TEST |
| IMPROVED NON-DEHISCENT TEST (Character No. 27) | ZZ | Eliminate from Sesaco: 11W, 19A, S22, S23, S24, S25, S26, S28, S29, S55 (all of these lines and varieties have been disclosed in previous patents, and there are no lines or varieties that are not included.) |
| | IND | From Sesaco: S27, S30, S32, and S70, go to PRESENCE OF PYGMY GENE |
| PRESENCE OF PYGMY GENE | NO | Eliminate from Sesaco: S27, S30, and S32 |
| | YES | S70. Go to Table IV to compare characters affected by the pygmy gene: HEIGHT OF PLANT (Character No 5), HEIGHT OF FIRST CAPSULE (Character No 6), and AVERAGE INTERNODE LENGTH WITHIN CAPSULE ZONE (Character No 9) |

[a] SHA = shattering; SSH = semi-shattering; ID = indehiscent; SR = shatter resistant; XX = not non-dehiscent according to the teachings of U.S. Pat. No. 6,100,452; ND = non-dehiscent according to the teachings of U.S. Pat. No. 6,100,452; ZZ = not Improved non-dhiscent; IND = improved non-dehiscent according to the teachings of U.S. patent application Ser. No. 12/041,257

Table IV compares the critical pygmy characters against the previously patented Sesaco varieties grown side by side in the 2008 Uvalde nursery in four replications. S70 is considerably shorter with a lower height of the first capsule, more capsule node pairs, and a shorter internode length than all previously developed Sesaco varieties.

TABLE IV

Comparison of S70 to previously patented sesame varieties

| No. | Character | S25 | S26 | S27 | S28 | S29 | S30 | S32 | S55 | S70 |
|---|---|---|---|---|---|---|---|---|---|---|
| 5 | HEIGHT OF PLANT (cm) | 123 | 135 | 124 | 126 | 124 | 131 | 145 | 123 | 85 |
| 6 | HEIGHT OF FIRST CAPSULE (cm) | 49 | 53 | 52 | 53 | 44 | 43 | 53 | 53 | 27 |
| 8 | NUMBER OF CAPSULE NODE PAIRS | 21 | 22 | 25 | 22 | 23 | 24 | 25 | 24 | 28 |
| 9 | AVERAGE INTERNODE LENGTH WITHIN CAPSULE ZONE (cm) | 3.5 | 3.8 | 2.9 | 3.4 | 3.5 | 3.6 | 3.6 | 3.0 | 2.1 |
| 10 | PRESENCE OF PYGMY GENE | NO | NO | NO | NO | NO | NO | NO | NO | YES |

Table V compares S70 to S26, S28, S30, S32, and S55, the current commercial varieties. When specified by year and nursery, the lines were grown side by side. The table is in terms of all of the characters listed in Table II. The major differences in Table V are indicated in the "Dif" column by a "C" for commercially important differences and an "M" for morphological differences.

TABLE V

Character Comparison of S26, S28, S30, S32, S55 and S70[a]

| No. | Character | | Year/nursery | S26 | S28 | S30 | S32 | S55 | S70 | Dif |
|---|---|---|---|---|---|---|---|---|---|---|
| 1 | Branching | genotype | All | B | B | U | B | B | B | |
|   | Style | phenotype | All | B | B | U | B | B | U | |
| 2 | Number of Capsules per Leaf Axil | | All | 1 | 1 | 1 | 1 | 1 | 1 | |
| 3 | Maturity Class | | Adjusted PM | 99 | 99 | 98 | 98 | 98 | 98 | |
|   |   | | 2005-2008 UV | M | M | M | M | M | | |
| 4 | Plant Phenotype | | All | B1M | B1M | U1M | B1M | B1M | U1M | |
| 5 | Height of Plant (cm) | | 2008 UV | 135 | 126 | 131 | 145 | 123 | 85 | C |
| 6 | Height of First Capsule (cm) | | 2008 UV | 53 | 53 | 43 | 53 | 53 | 27 | C |
| 7 | Capsule Zone Length (cm) | | 2008 UV | 81 | 72 | 88 | 91 | 70 | 58 | C |
| 8 | Number of Capsule Node pairs | | 2008 UV | 22 | 22 | 24 | 25 | 24 | 28 | C |
| 9 | Average Internode Length within Capsule Zone (cm) | | 2008 UV | 3.8 | 3.4 | 3.6 | 3.6 | 3.0 | 2.1 | C |
| 10 | Presence of pygmy alleles | | All | No | No | No | No | No | Yes | C |
| 11 | Yield at Drydown (kg/ha) | | 2008 UV | 1,429 | 1,381 | 1,474 | 1,556 | 1,253 | 1,220 | C |
|   |   | | 2008 LO | 429 | 511 | 676 | 593 | 514 | 742 | C |
| 12 | Resistance to Drought | | 2000 SA | Good | Good | NT | NT | NT | NT | |
| 13 | Leaf Length (cm) | | 5th - 2008 UV | 28.1 | 23.0 | 16.3 | 25.5 | 20.7 | 14.3 | M |
|   |   | | 10th - 2008 UV | 22.3 | 18.0 | 18.5 | 18.3 | 19.7 | 15.6 | M |
|   |   | | 15th - 2008 UV | 15.9 | 13.7 | 15.0 | 14.1 | 14.5 | 13.6 | |
| 14 | Leaf Blade Length (cm) | | 5th - 2008 UV | 16.6 | 13.8 | 10.7 | 14.8 | 13.6 | 10.2 | |
|   |   | | 10th - 2008 UV | 16.8 | 14.4 | 14.3 | 14.7 | 15.4 | 13.2 | M |
|   |   | | 15th - 2008 UV | 13.3 | 11.5 | 12.5 | 12.2 | 11.9 | 11.5 | |
| 15 | Leaf Blade Width (cm) | | 5th - 2008 UV | 23.0 | 18.0 | 10.5 | 13.8 | 10.0 | 6.0 | M |
|   |   | | 10th - 2008 UV | 5.4 | 3.6 | 3.0 | 3.0 | 4.1 | 3.3 | |
|   |   | | 15th - 2008 UV | 2.6 | 2.0 | 2.0 | 1.6 | 2.7 | 2.2 | |
| 16 | Petiole Length (cm) | | 5th - 2008 UV | 11.5 | 9.2 | 5.6 | 10.7 | 7.1 | 4.1 | M |
|   |   | | 10th - 2008 UV | 5.5 | 3.6 | 4.2 | 3.6 | 4.3 | 3.3 | |
|   |   | | 15th - 2008 UV | 2.6 | 2.3 | 2.4 | 2.0 | 2.6 | 2.2 | |
| 17 | Number of Carpels per Capsule | | All | 2 | 2 | 2 | 2 | 2 | 2 | |
| 18 | Capsule Length (cm) | | 1997-2008 All | 2.25 | 2.26 | 2.27 | 2.13 | 2.40 | 2.11 | |
| 19 | Seed Weight per Capsule (g) | | 1997-2008 All | 0.233 | 0.227 | 0.260 | 0.228 | 0.211 | 0.221 | |
| 20 | Capsule Weight per Capsule (g) | | 1997-2008 All | 0.162 | 0.162 | 0.167 | 0.147 | 0.149 | 0.133 | M |
| 21 | Capsule Weight per cm of Capsule (g) | | 1997-2008 All | 0.072 | 0.072 | 0.073 | 0.069 | 0.062 | 0.063 | |
| 22 | Visual Seed Retention | | All | W | W | I | I | W | I | C |
| 23 | Shaker Shatter Resistance (%) | | 1997-2008 All | 73.0 | 75.0 | 77.8 | 75.8 | 70.8 | 77.4 | C |
| 24 | Capsule Shattering Type | | All | SR | SR | SR | SR | SR | SR | |
| 25 | Non-dehiscent Test | | All | ND | ND | ND | ND | ND | ND | |
| 26 | Improved Non-dehiscent visual rating | | 2008 UV | 6.5 | 6.2 | 7.2 | 7.0 | 6.8 | 7.5 | C |
|   |   | | 2008 LO | 6.3 | 6.3 | 7.4 | 7.2 | 7.0 | 7.4 | C |
| 27 | Improved Non-dehiscent Test | | All | ZZ | ZZ | IND | IND | ZZ | IND | C |
| 28 | Days to Flowering | | 2008 UV | 50 | 48 | 36 | 38 | 40 | 38 | |
| 29 | Days to Flower Termination | | 2008 UV | 83 | 82 | 75 | 77 | 77 | 74 | |
| 30 | Days to Physiological Maturity | | 2008 UV | 110 | 109 | 101 | 106 | 99 | 98 | C |
| 31 | Days to Direct Harvest | | 2008 UV | 146 | 146 | 139 | 141 | 149 | 141 | |
| 32 | Lodging Resistance | | 2007 UV | 6.6 | 7.0 | 7.3 | 6.2 | 7.4 | 7.3 | C |
|   |   | | 2007 LO | 5.0 | 5.3 | 7.9 | 7.1 | 8.0 | 8.0 | C |
| 33 | Seed Color | | All | BF | BF | BF | BF | BLK | BF | C |
| 34 | Seed Weight - 100 Seeds from 10 cap test (g) | | 1997-2008 All | 0.330 | 0.329 | 0.317 | 0.311 | 0.328 | 0.326 | C |
| 35 | Composite Kill Resistance | | 2008 UV | 7.3 | 7.3 | 6.9 | 6.5 | 6.8 | 7.2 | C |
| 36 | Resistance to Fusarium Wilt (F. oxysporum) | | | NT | NT | NT | NT | NT | NT | |
| 37 | Resistance to Phytophtora Stem Rot (P. parasitica) | | | NT | NT | NT | NT | NT | NT | |
| 38 | Resistance to Charcoal Rot (Macrophomina phaseoli) | | | NT | NT | NT | NT | NT | NT | |
| 39 | Resistance to Bacterial Black Rot (Pseudomonas sesami) | | 2004 UV | 7.0 | 7.0 | 8.0 | 8.0 | NT | NT | |
| 40 | Resistance to Silverleaf Whitefly (Bemisia argentifolii) | | 2007 UV | NEC | NEC | NEC | NEC | NEC | NEC | |
| 41 | Resistance to Green Peach Aphid (Myzus persica) | | 2004 UV | 8.0 | 7.9 | 8.0 | 5.5 | NT | NT | |
| 42 | Resistance to Pod Borer (Heliothis spp.) | | 2001 UV | NEC | NT | NT | NT | NT | NT | |

TABLE V-continued

Character Comparison of S26, S28, S30, S32, S55 and S70[a]

| No. | Character | Year/nursery | S26 | S28 | S30 | S32 | S55 | S70 | Dif |
|---|---|---|---|---|---|---|---|---|---|
| 43 | Resistance to Army Worms (*Spodoptera* spp.) | | NT | NT | NT | NT | NT | NT | |
| 44 | Resistance to Cabbage Loopers (*Pieris rapae*) | 2007 UV | NEC | NEC | NEC | NEC | NEC | NEC | |

[a]B = true branches;
U = uniculm (no true branches);
UV = Uvalde nursery;
M = medium maturity class of 95-104 days;
B1M = phenotype of true branches, single capsules per leaf axil, and medium maturity class of 95-104 days;
U1M = phenotype of uniculm, single capsules per leaf axil, and medium maturity class of 95-104 days;
LO = Lorenzo nursery;
NT = not tested;
W = weather visual seed retention >75%;
SR = shatter resistant;
ND = non-dehiscent;
ZZ = not improved non-dehiscent;
IND = improved non-dehiscent;
BF = buff color;
BLK = black color; and
NEC = no economic damage - not enough disease or insects to do ratings.

The characters SHAKER SHATTER RESISTANCE (Character No. 23), IMPROVED NON-DEHISCENT VISUAL RATING (Character No. 26), HEIGHT OF PLANT (Character No. 5), HEIGHT OF FIRST CAPSULE (Character No. 6), CAPSULE ZONE LENGTH (Character No. 7), NUMBER OF CAPSULE NODE PAIRS (Character No. 8), AVERAGE INTERNODE LENGTH WITHIN CAPSULE ZONE (Character No. 9), PRESENCE OF PYGMY ALLELES (Character No. 10), COMPOSITE KILL RESISTANCE (Character No. 35), DAYS TO PHYSIOLOGICAL MATURITY (Character No. 30), YIELD AT DRYDOWN (Character No. 11), LODGING RESISTANCE (Character No. 32), SEED COLOR (Character No. 33), and SEED WEIGHT—100 SEEDS FROM 10CAP TEST (Character No. 34) will be discussed further below with respect to the patented varieties S25, S26, S27, S28, S29, S30, S32, and S55.

Figure 2:
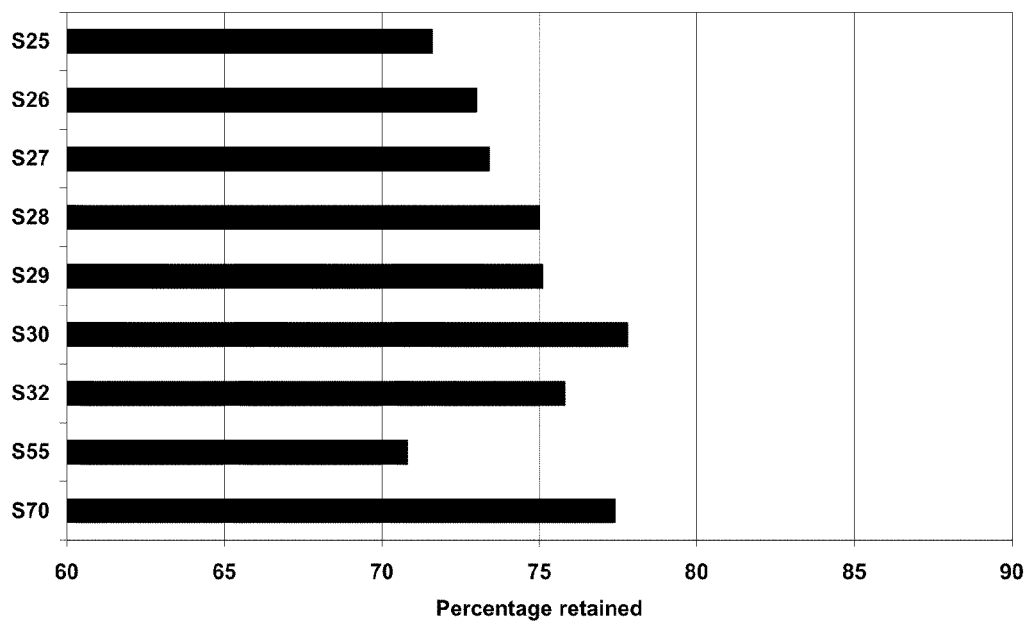
FIGS. 2 through 11 compare Sesaco 70 (S70) to the Sesaco patented varieties: Sesaco 25 (S25), Sesaco 26 (S26), Sesaco 27 (S27), Sesaco 28 (S28), Sesaco 29 (S29), Sesaco 30 (S30), Sesaco 32 (S32), and Sesaco 55 (S55).

FIG. 2 provides the SHAKER SHATTER RESISTANCE (Character No. 23). The varieties patented have SHAKER SHATTER RESISTANCE in the low to high 70s. Selection criteria for 10cap testing are based in VISUAL SEED RETENTION (Character No. 22). The 10cap testing provides the SHAKER SHATTER RESISTANCE percentages. The S70 SHAKER SHATTER RESISTANCE is close to S30 and higher than the other commercial varieties.

Figure 3:
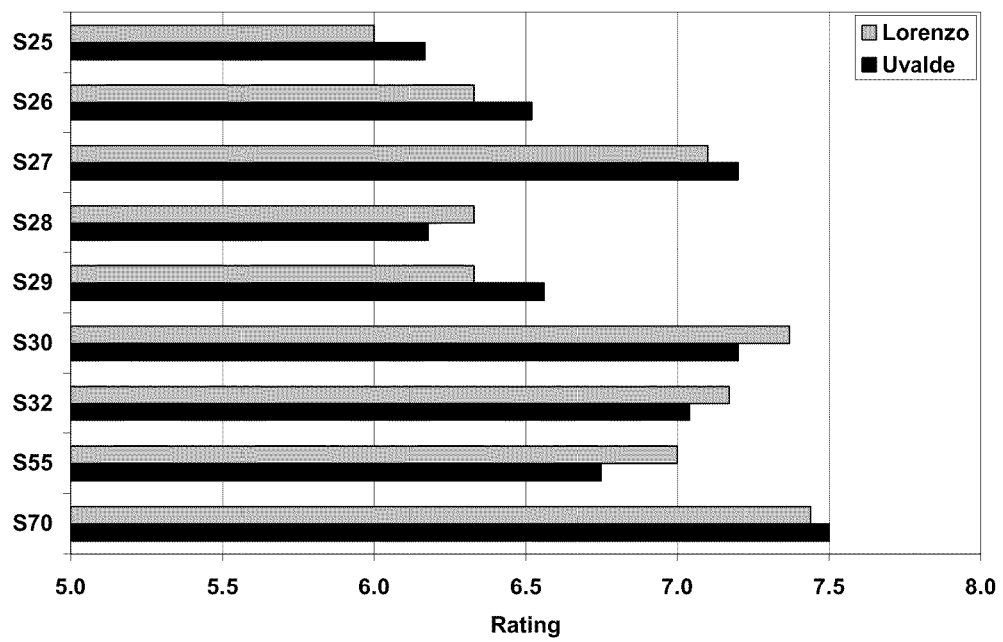

FIG. 3 provides the IMPROVED NON-DEHISCENT VISUAL RATING (Character No. 26) which provides the data for the IMPROVED NON-DEHISCENT TEST (Character No. 27). SHAKER SHATTER RESISTANCE (Character No. 23) represents the amount of seed that is retained by the plant several months after being dry in the field. This standard was developed as a minimum standard in 1997-1998 and has proven to be a good predictor of shatter resistance. However, when the plants have reached DAYS TO DIRECT HARVEST (Character No. 31), the plants are holding more than the seed represented by the SHAKER SHATTER RESISTANCE percentage. If there is no rain, fog, dew, or wind during the drying phase, the plants will be retaining almost all of their seed for the combine. However, in the United States, rain and wind are prevalent in the Fall as the sesame is drying. From the time that a capsule is dry, the amount of shatter resistance begins to deteriorate. The IMPROVED NON-DEHISCENT VISUAL RATING sets a new benchmark for selecting varieties: the line has to have a rating of 7 or higher 4 weeks after DAYS TO DIRECT HARVEST (the ideal harvest time). S30, S32, and S70 are the only commercial varieties that meet this new standard as shown in FIG. 3 which compared the patented varieties in a side by side comparison in two nurseries in 2008.

Figure 4:
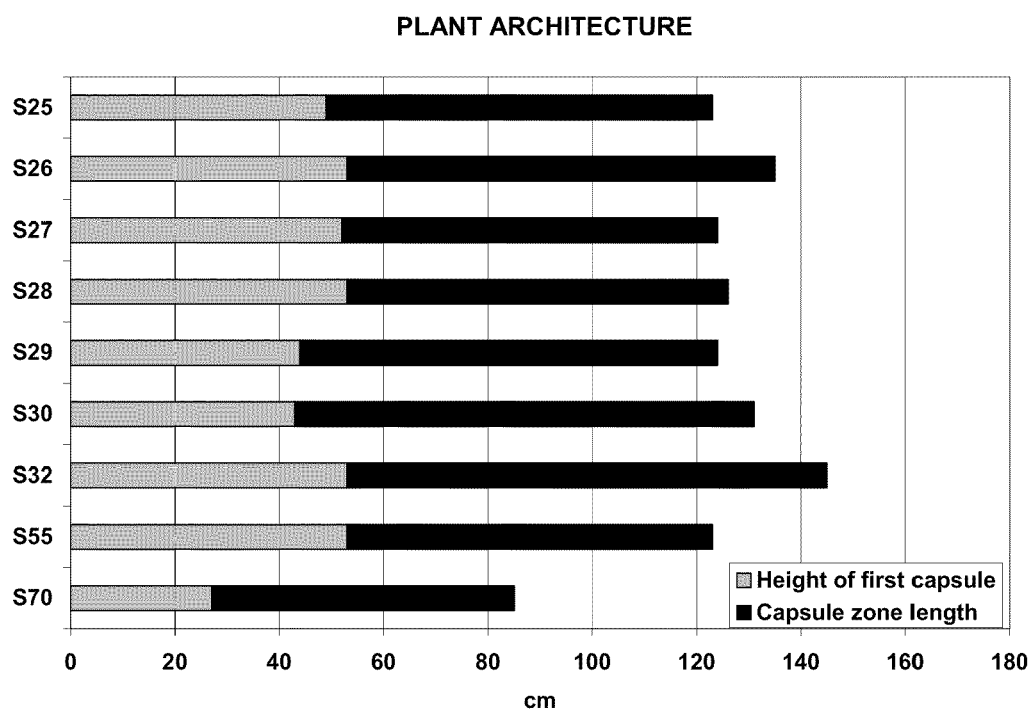

FIG. 4 provides the plant architecture by depicting the HEIGHT OF THE FIRST CAPSULE (Character No. 6) and the CAPSULE ZONE LENGTH (Character No. 7). Together, these add up to the HEIGHT OF PLANT (Character No. 5). The PRESENCE OF PYGMY ALLELES (Character No. 10) determines the expression of these three characters. The HEIGHT OF PLANT is important in combining the crop in that when plants are tall, the reel on the header will push the plants forward before pulling them back into the header. This rough handling of the plants shakes seed out in front of the combine which falls to the ground before the header can reach the falling seed. With the short HEIGHT OF PLANT of S70, the reel pulls the plants into the header without pushing them away first, and thus, there is less shattering in front of the combine. Although the HEIGHT OF FIRST CAPSULE is shorter than the rest of the varieties, there is still enough space for the combine header to get under the lowest capsule in most environments. The exception is hilly terrain which to a certain extent also affects the other varieties.

Figure 5:
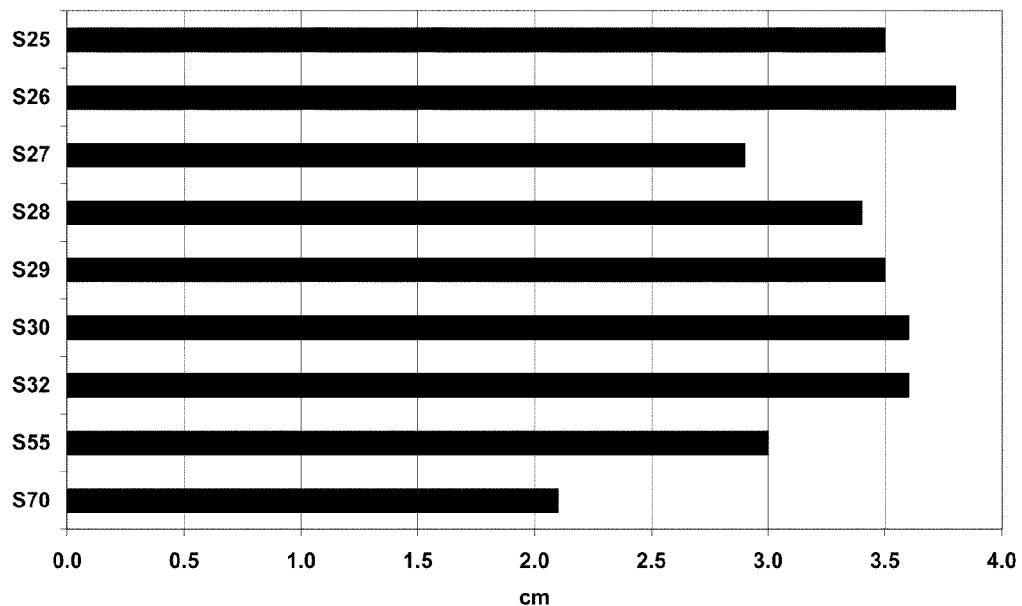
Figure 6:
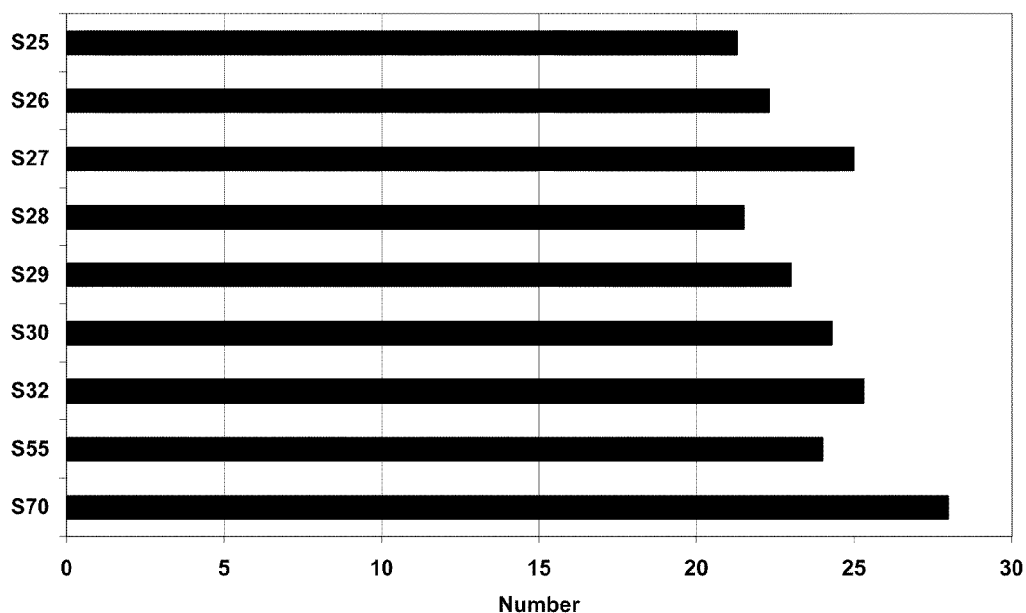

FIG. 5 provides the AVERAGE INTERNODE LENGTH WITHIN CAPSULE ZONE (Character No. 9). In the world germplasm there are many short lines that do not have commercially suitable yields because the short height limits the amount of production on the plant. The pygmy gene shortens the AVERAGE INTERNODE LENGTH WITHIN CAPSULE ZONE allowing a higher NUMBER OF CAPSULE NODE PAIRS (Character No. 8). S70 has a higher number of node pairs than the patented varieties as shown in FIG. 6 comparing the lines in a side-by-side comparison. The pygmy alleles allow for this higher number, but not all pygmy lines have a higher number. Conversely, there are very tall lines that have more node pairs than S70, but these lines are difficult to combine because of their HEIGHT OF PLANT.

Figure 7:
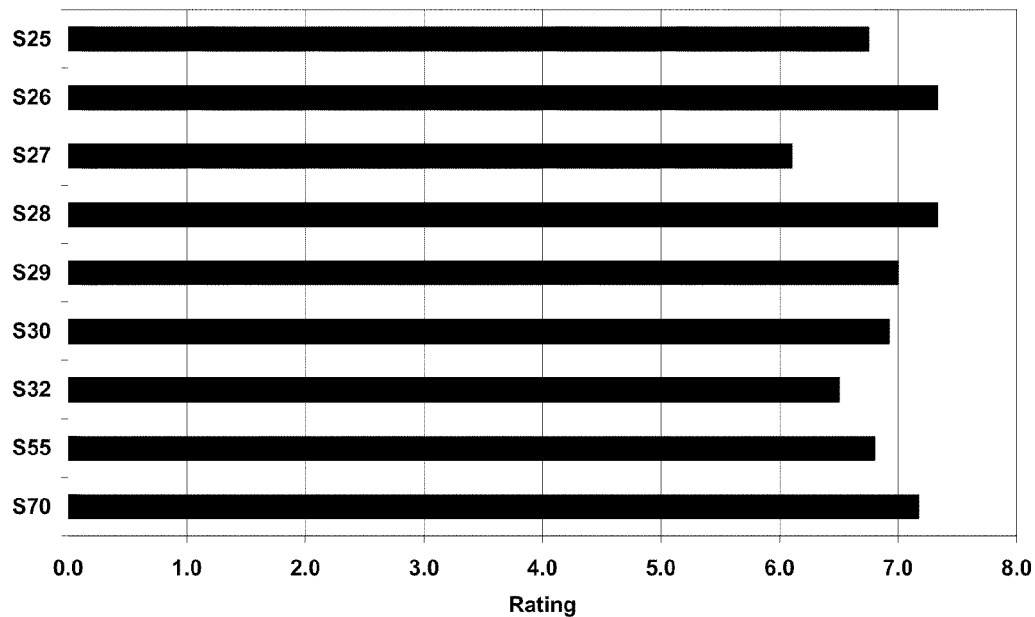

FIG. 7 provides the COMPOSITE KILL RESISTANCE (Character No. 35). COMPOSITE KILL RESISTANCE is a composite rating of resistance to three root rots: *Fusarium*, *Phytophtora*, and *Macrophomina*. In most years, Fusarium is the major cause of kill. When sesame is first introduced into a growing area, there are few disease problems, but over time the spores of these fungi accumulate, and disease resistance becomes important. When sesame was first introduced in Uvalde in 1988, the yields were high. As farmers planted on the same fields in subsequent years, the yields decreased. S70 has a commercially acceptable COMPOSITE KILL RESISTANCE and better than all but 2 of the patented varieties.

Figure 8:
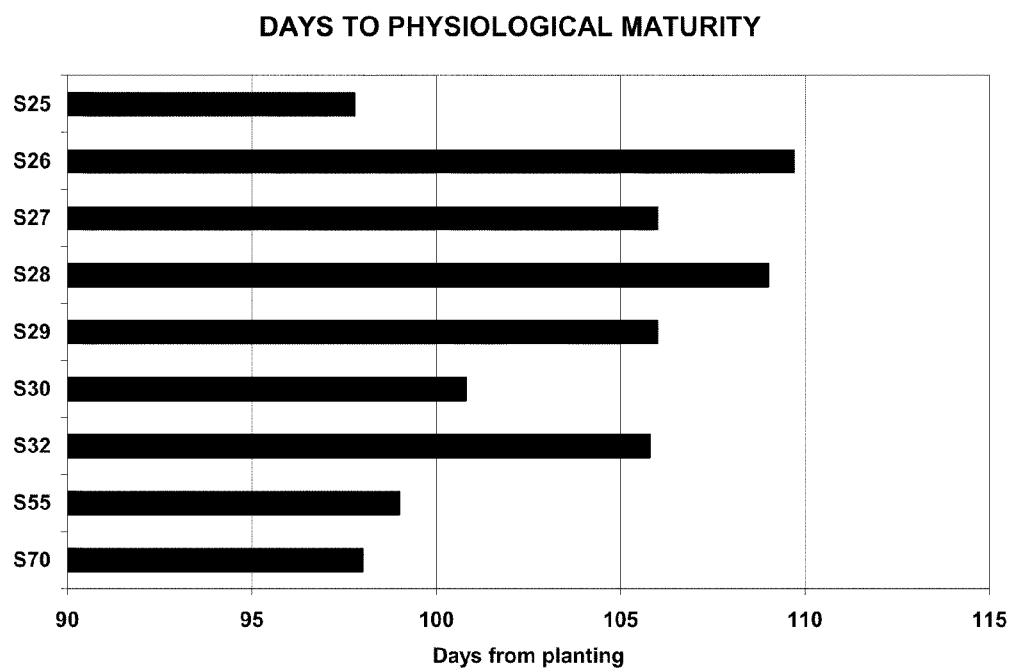

FIG. 8 provides the mean DAYS TO PHYSIOLOGICAL MATURITY (Character No. 30). In the United States, sesame is currently grown from South Texas to mid Kansas. The growing window of a crop is determined by the earliest the crop can be planted in the spring as the ground warms up, and the onset of cold weather in the fall. Current sesame varieties require about 21° C. ground temperature to establish an adequate population. In most years, the ground is warm enough in South Texas in middle April and in southern Kansas in late May. Current sesame varieties require night temperatures above 5° C. for normal termination. In most years, the night temperatures are warm enough in South Texas until middle November and in southern Kansas until middle October. There have been years when cold fronts affect the growth of sesame in the middle of September in the north. East of Lubbock, Tex., the elevations begin climbing towards the Rocky Mountains, and there are later warm temperatures in the spring and earlier cold temperatures in the fall. In all years, if the sesame is planted as early as temperatures allow, lines with DAYS TO PHYSIOLOGICAL MATURITY of 105 days or less will have no problems. However, most areas are rainfed, and it is essential to have a planting rain before planting the sesame. Thus, the earlier the DAYS TO PHYSIOLOGICAL MATURITY of the variety, the more flexibility the farmers have with planting date. The DAYS TO PHYSIOLOGICAL MATURITY for S70 is 98 days which allows it to be planted in all of the current sesame growing areas. It also comparable to the S25 variety which was the earliest commercial ND variety in the United States.

Figure 9:
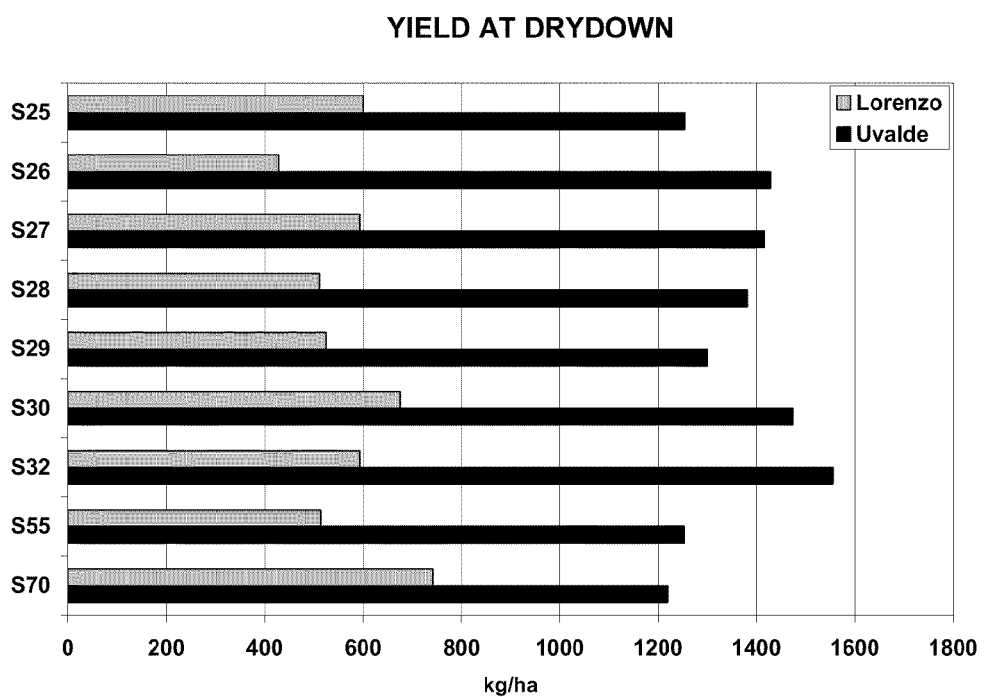

FIG. 9 provides the mean YIELD AT DRYDOWN (Character 11) in Uvalde and Lorenzo in 2008. In releasing a new variety, another important consideration is whether the yields (YIELD AT DRYDOWN) will be comparable or better than the existing varieties. The yields of S70 are lower than most of the current commercial varieties in Uvalde and other areas with high moisture, but in areas with low moisture such as Lorenzo, S70 has outyielded the other commercial lines for the past three years. By being shorter, S70 devotes less resources to making stems, leaves, and capsules, and is able to direct the scarce moisture into making more seed.

Figure 10:
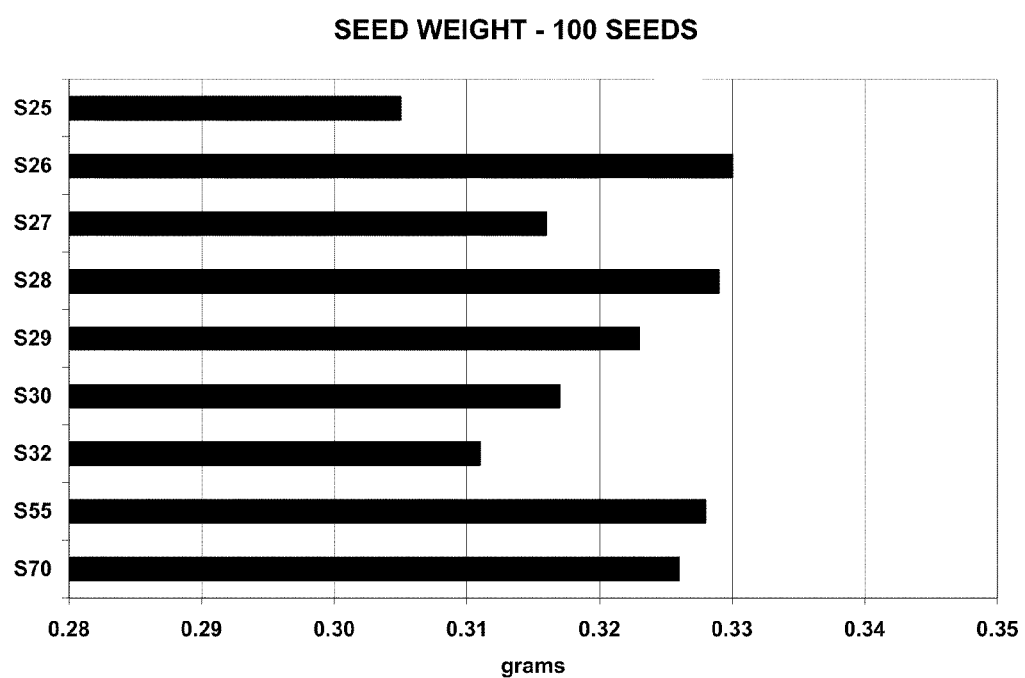

FIG. 10 provides the mean SEED WEIGHT—100 SEEDS FROM THE 10CAP TEST (Character No. 34). For the past 30 years, the lower threshold for seed size in the U.S. markets has been 0.30 g. All of the patented varieties surpass this threshold. The hulled market is the premium use of sesame in the United States and Europe. In recent years, hulled sesame processors have been increasing the specifications of SEED WEIGHT—100 SEEDS FROM THE 10CAP TEST to between 0.33 and 0.35 g, with the larger seed preferable for hulled products used on top of breads and buns. To date, the Sesaco varieties with the highest SEED WEIGHT—100 SEEDS FROM THE 10CAP TEST have had marginal SHAKER SHATTER RESISTANCE (Character No. 23) and poor COMPOSITE KILL RESISTANCE (Character No. 35). Most markets have no specifications on seed weight, but larger seed is still desirable. The mean SEED WEIGHT—100 SEEDS FROM THE 10CAP TEST for S70 is comparable to the premier seed of S26 and S28 and meets the specifications for the majority of the U.S. market.

Figure 11:
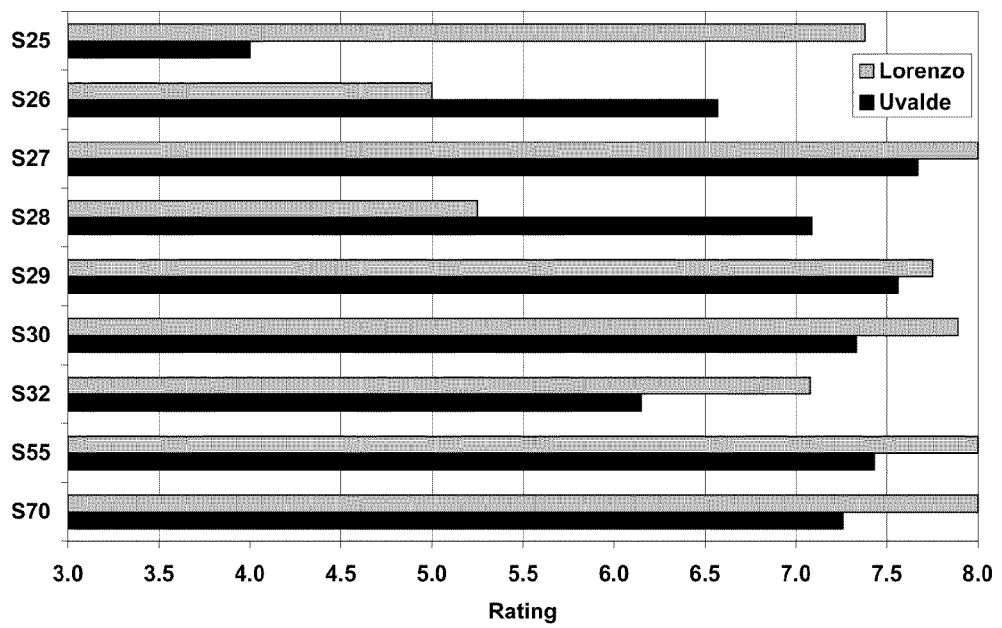

FIG. 11 provides the LODGING RESISTANCE (Character No. 32). In the United States sesame growing areas there are strong winds that affect all crops. The wind speed is dependent on the height from the ground with lower speeds closer to the ground. With a low HEIGHT OF PLANT (Character No. 5) S70 sesame presents a lower profile to the wind and thus has a good rating for lodging.

SEED COLOR (Character No. 33) is the last important character and S70 is the same (buff) as the other commercial varieties.

The leaf dimensions (LEAF LENGTH—Character No. 13, LEAF BLADE LENGTH—Character No. 14, LEAF BLADE WIDTH—Character No. 15, and PETIOLE LENGTH—Character No. 16) are somewhat smaller than previously developed ND and IND varieties. However, it has been found that the leaf area is adequate for photosynthesis required to produce a commercially suitable yield. The CAPSULE WEIGHT PER CAPSULE (Character No. 24) is morphologically different from the other varieties in Table V. However, though useful for morphology the capsule weight per capsule does not provide a commercially significant variable.

S70 exhibits similar values for other characteristics noted or tested for ND and IND varieties, except those discussed above.

On May 14, 2008, a deposit of at least 2500 seeds of sesame plant S70 was made by Sesaco Corporation under the provisions of the Budapest Treaty with the American Type Culture Collection (ATCC), 10801 University Boulevard, Manassas, Va. 20110-2209, and the deposit was given ATCC Accession No. PTA-9272. This deposit will be maintained in the ATCC depository for a period of 30 years or 5 years after the last request or for the enforceable life of the patent, whichever is longer. Should the seeds from the sesame line S70 deposited with the American Type Culture Collection become nonviable, the deposit will be replaced by Sesaco Corporation upon request.

The foregoing invention has been described in some detail by way of illustration and characters for purposes of clarity and understanding. However, it will be obvious that certain changes and modifications may be practiced within the scope of the invention as limited only by the scope of the appended claims.

I claim:

1. A seed of sesame variety designated S70, a sample of said seed having been deposited under ATCC Accession No. PTA-9272.

2. A sesame plant produced by growing the seed of sesame variety S70, a sample of said seed having been deposited under ATCC Accession No. PTA-9272.

3. Pollen of said sesame plant of claim 2.

4. A sesame plant having all the physiological and morphological characteristics of sesame variety S70, a sample of the seed of said variety having been deposited under ATCC Accession No. PTA-9272.

5. A tissue culture of regenerable cells produced from seed of sesame variety S70, a sample of said seed having been deposited under ATCC Accession No. PTA-9272.

6. A tissue culture of regenerable cells produced from sesame plant S70 produced by growing the seed of sesame variety S70, a sample of said seed having been deposited under ATCC Accession No. PTA-9272.

7. A sesame plant regenerated from a tissue culture of regenerable cells produced from seed of sesame variety S70, a sample of said seed having been deposited under ATCC Accession No. PTA-9272, wherein said regenerated sesame plant has all the physiological and morphological characteristics of said sesame variety S70.

8. A sesame plant regenerated from a tissue culture of regenerable cells produced from a sesame plant produced by growing the seed of sesame variety S70, a sample of said seed having been deposited under ATCC Accession No. PTA-9272, wherein said regenerated sesame plant has all the physiological and morphological characteristics of said sesame variety S70.

9. A method of producing sesame seed, comprising crossing a first parent sesame plant with a second parent sesame plant and harvesting the resultant sesame seed, wherein said first or second parent sesame plant was produced by growing seed of sesame variety S70, a sample of said seed having been deposited under ATCC Accession No. PTA-9272.

* * * * *

UNITED STATES PATENT AND TRADEMARK OFFICE
CERTIFICATE OF CORRECTION

PATENT NO. : 8,058,503 B1
APPLICATION NO. : 12/769495
DATED : November 15, 2011
INVENTOR(S) : Derald Ray Langham It is certified that error appears in the above-identified patent and that said Letters Patent is hereby corrected as shown below:

Col. 4, line 34, replace ""phenology"" with -- "phenology," --
Col. 5, line 17, replace "sesame is" with -- sesame, is --
Col. 5, line 28, replace "capsules is" with -- capsules --
Col. 8, line 58, replace "because" with -- became --
Col. 11, Table II, under "Rating," column text line 38, after "1982-2001" insert -- (Total number --
Col. 12, Table II, under "Methodology," column text line 53, before "adequate moisture" delete "(Total number"
Col. 13, Table II, under "Rating," column text line 66, after "1999-2001" insert -- (Total number --
Col. 14, Table II, under "Methodology," column text line 44, before "on the amount" delete "(Total number"
Col. 15, Table II, under "Rating," column text line 50, after "1999-2001" insert -- (Total number --
Col. 16, Table II, under "Methodology," column text line 37, before "node pairs" delete "(Total number"
Col. 20, Table II, under "Methodology," column text line 40, replace "Character No. 14)" with -- (Character No. 14) --
Col. 25, Table II, under "Rating," column text lines 13-14, replace "(unit of measure: actual number" with -- (unit of measure: actual number) --
Col. 29, Table II, under "Character," column text line 12, delete "Character"
Col. 29, Table II, under "Rating," column text line 31, delete "Rating"
Col. 30, Table II, under "Methodology," column text line 31, replace "'total seed." with -- 'total seed.' --
Col. 30, Table II, under "Methodology," column text line 59, delete "Methodology"
Col. 31, Table II, under "Character," column text line 4, delete "Character"
Col. 31, Table II, under "Rating," column text line 9, delete "Rating"
Col. 32, Table II, under "Methodology," column text line 3, replace "dry down" with -- drydown --
Col. 32, Table II, under "Methodology," column text line 23, delete "Methodology"
Col. 32, Table II, under "Methodology," column text line 37, replace "counts" with -- count --
Col. 33, Table II, under "Rating," column text line 5, replace "all nurseries" with -- all nurseries) --
Col. 33, Table II, under "Character," column text line 17, delete "Character"

Signed and Sealed this
Sixteenth Day of October, 2012

David J. Kappos
*Director of the United States Patent and Trademark Office*

CERTIFICATE OF CORRECTION (continued)
U.S. Pat. No. 8,058,503 B1

Col. 33, Table II, under "Rating," column text line 21, delete "Rating"
Col. 34, Table II, under "Methodology," column text line 6, delete "Methodology"
Col. 35, Table II, under "Rating," column text line 9, replace "102.2" with -- <102.2 --
Col. 35, Table II, under "Rating," column text line 24, replace "tthrough" with -- through) --
Col. 35, Table II, under "Rating," column text line 31, replace "3 =" with -- 3 = <137.8 days; 32.1% --
Col. 35, Table II, under "Rating," column text line 32, replace "4 =" with -- 4 = <149.4 days; 44.2% --
Col. 35, Table II, under "Rating," column text line 33, replace "5 =" with -- 5 = >149.3 days; 7.2% --
Col. 36, Table II, under "Methodology," column text line 4, delete "C"
Col. 37, Table II, under "Rating," column text line 24, replace "0/0" with -- % --
Col. 38, Table II, under "Methodology," column text line 63, replace "brown light gray and" with -- brown, light gray and --
Col. 39, Table II, under "Rating," column text line 24, replace "<0..251" with -- <0.251 --
Col. 41, Table II, under "Rating," column text line 24, delete "COMMENTS: Macrophomina has been"
Col. 41, Table II, under "Character," column text line 20, replace "sesame)" with -- sesami) --
Col. 42, Table II, under "Methodology," column text line 3, after "longer increasing" insert -- . --
Col. 42, Table II, under "Methodology," column text line 25, after "(Character No. 36)", insert -- COMMENTS: Macrophomina has been --
Col. 48, Table III, under "Name cultivars tested by Sesaco," column text line 7, replace "included." with -- included.) --
Col. 48, Table III, under "Name cultivars tested by Sesaco," column text line 16, replace "(Character No 5)" with -- (Character No. 5) --
Col. 48, Table III, under "Name cultivars tested by Sesaco," column text line 18, replace "(Character No 6)" with -- (Character No. 6) --
Col. 48, Table III, under "Name cultivars tested by Sesaco," column text line 21, replace "(Character No 9)" with -- (Character No. 9) --
Col. 48, Table III, line 35 (in footnotes), replace "non-dhiscent;" with -- non-dehiscent; --
Col. 51, Table V, under "Year/nursery," row labeled 44, replace "2007 UV" with -- 2007 LO --
Col. 53, line 36, replace "variety which" with -- variety, which --